US007699818B2

(12) United States Patent
Gilbert

(10) Patent No.: US 7,699,818 B2
(45) Date of Patent: *Apr. 20, 2010

(54) INSERTION SYSTEM AND METHODS FOR NASOGASTRIC TUBES

(75) Inventor: Paul J. Gilbert, 57 E. Delaware Pl., # 3406, Chicago, IL (US) 60611-1632

(73) Assignee: Paul J. Gilbert, Payson, AZ (US)

( * ) Notice: Subject to any disclaimer, the term of this patent is extended or adjusted under 35 U.S.C. 154(b) by 18 days.

This patent is subject to a terminal disclaimer.

(21) Appl. No.: 11/769,597

(22) Filed: Jun. 27, 2007

(65) Prior Publication Data

US 2008/0004598 A1    Jan. 3, 2008

Related U.S. Application Data

(63) Continuation-in-part of application No. 11/548,086, filed on Oct. 10, 2006, which is a continuation-in-part of application No. 11/347,481, filed on Feb. 3, 2006.

(60) Provisional application No. 60/650,806, filed on Feb. 8, 2005.

(51) Int. Cl.
*A61M 31/00* (2006.01)
(52) U.S. Cl. ............ 604/270; 604/103.04; 604/164.13; 604/165.01
(58) Field of Classification Search ............ 604/103.04, 604/164.13, 165.01, 265, 270, 275
See application file for complete search history.

(56) References Cited

U.S. PATENT DOCUMENTS

| 2,657,691 | A | | 11/1953 | Nordstrom, Jr. |
| 4,735,214 | A | | 4/1988 | Berman et al. |
| 4,819,619 | A | * | 4/1989 | Augustine et al. ...... 604/170.01 |
| 4,887,997 | A | | 12/1989 | Okada et al. |
| 5,318,530 | A | * | 6/1994 | Nelson, Jr. .................. 604/270 |
| 5,334,167 | A | * | 8/1994 | Cocanower ................. 604/523 |
| 5,391,158 | A | | 2/1995 | Peters et al. |
| 5,611,787 | A | * | 3/1997 | Demeter et al. ............. 604/270 |
| 2004/0039350 | A1 | | 2/2004 | McKittrick |

FOREIGN PATENT DOCUMENTS

JP        2002 191552 A        7/2002

* cited by examiner

*Primary Examiner*—Kevin C Sirmons
*Assistant Examiner*—Elizabeth R Moulton
(74) *Attorney, Agent, or Firm*—Carmen B. Patti; Carmen Patti Law Group, LLC

(57) ABSTRACT

A nasogastric tube insertion system comprises a nasogastric tube, a guide element, and an inserter element. The inserter element has a slim, elongate main body, a handle attached to the body, and an anatomically curved insertion section. The guide element comprises a swallowable weight attached to a cord, string, monofilament line, tube, or other similar line. The swallowable weight may be ablative in the presence of stomach fluids or may be deflated to allow the guide element to be removed while the nasogastric tube remains in place. The inserter element is inserted through the patient's nasal passages and optionally into the oropharynx. The weight is released and the patient swallows it into the stomach. The guide element is threaded through the guide element retaining structure, and the nasogastric tube is safely inserted along the guide element into the patient's stomach. Chemical property indicators sensitive to fluids found in the stomach may be provided in the nasogastric tube or the guide element to verify correct placement of the nasogastric tube in the stomach.

31 Claims, 23 Drawing Sheets

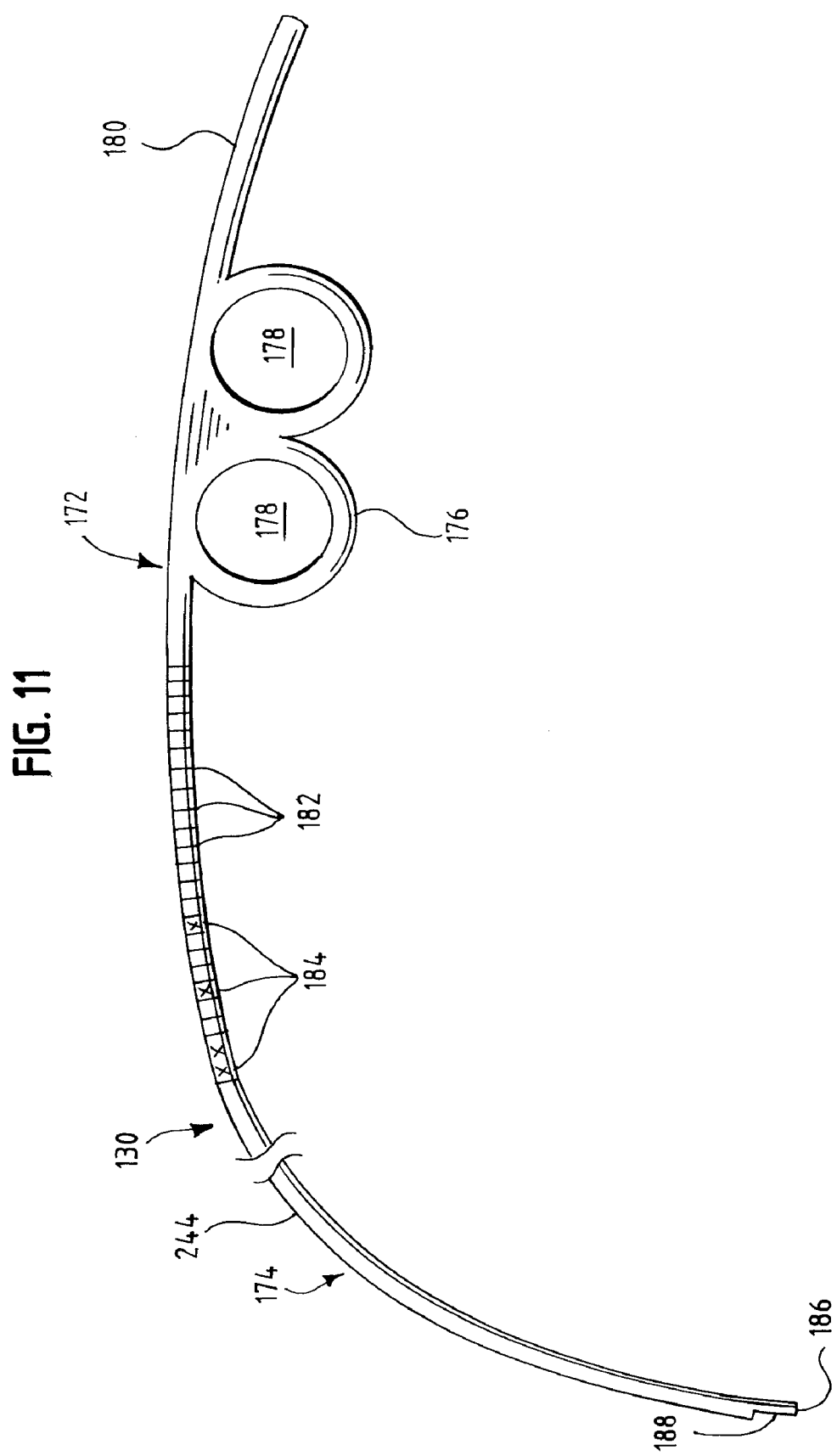

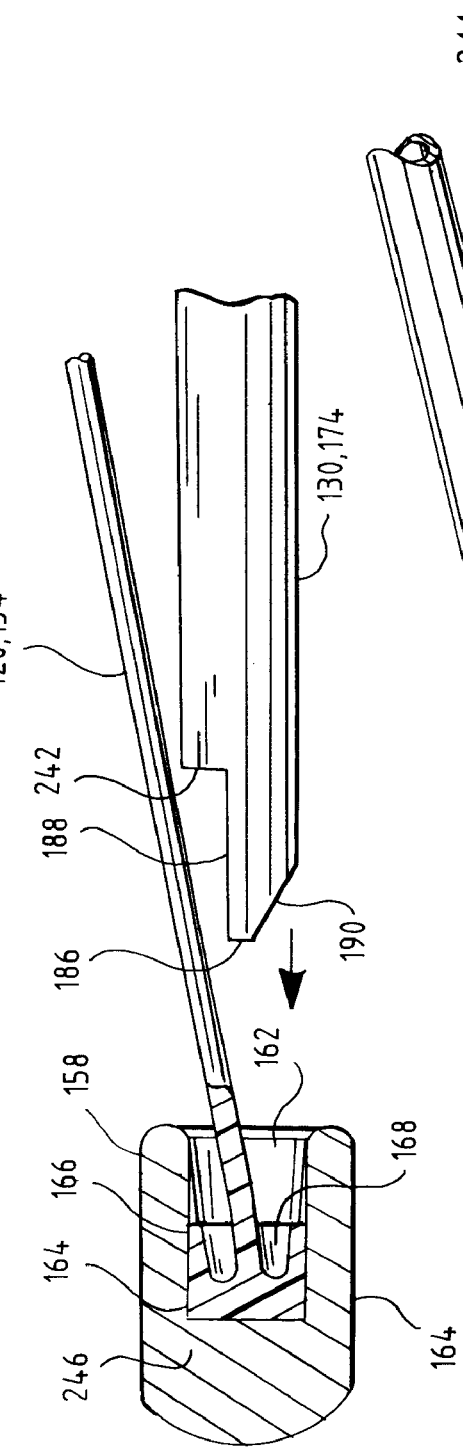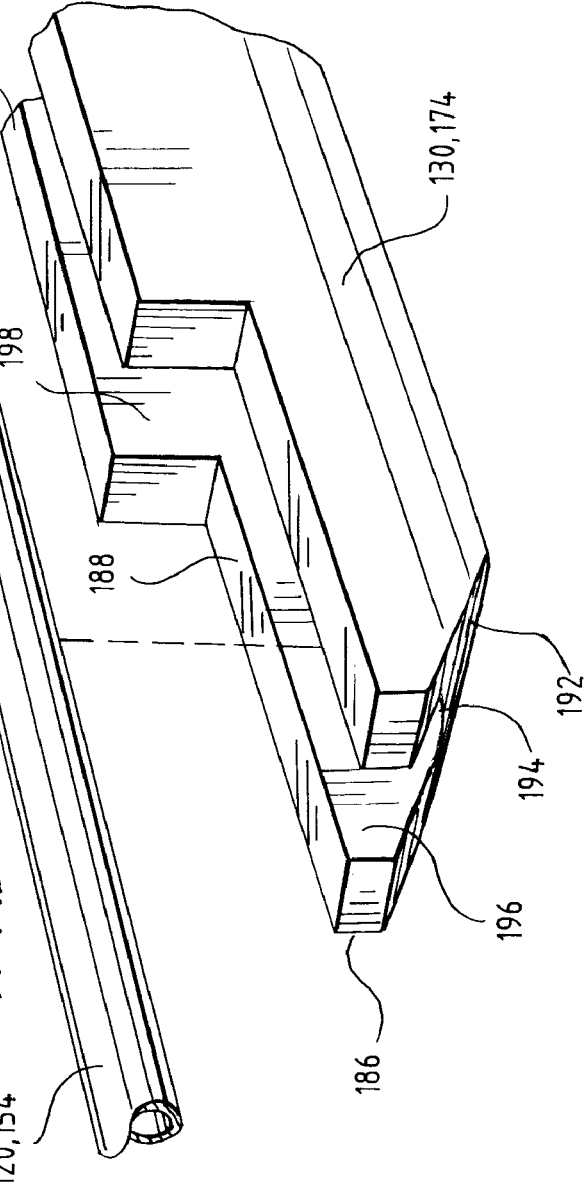

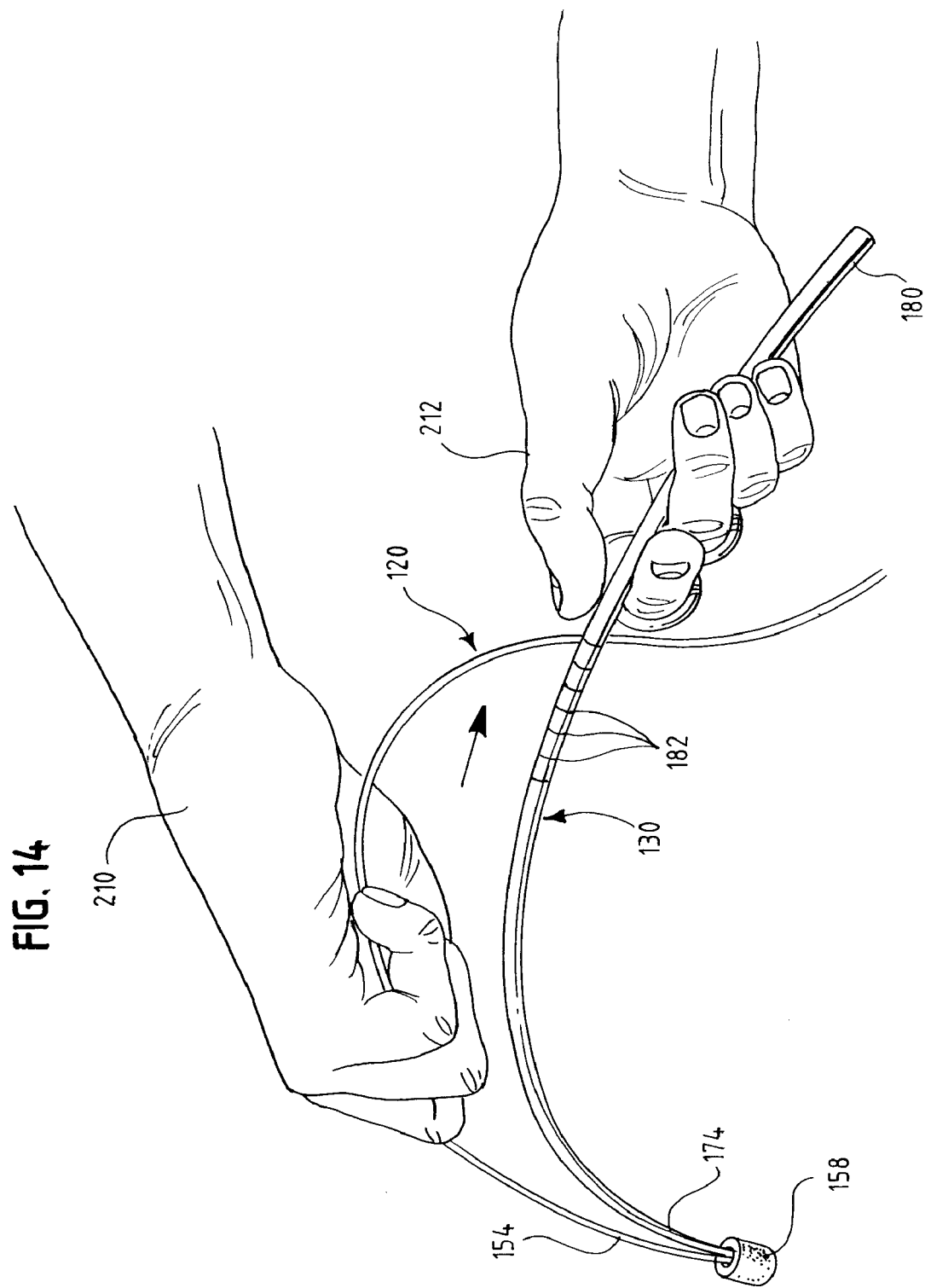

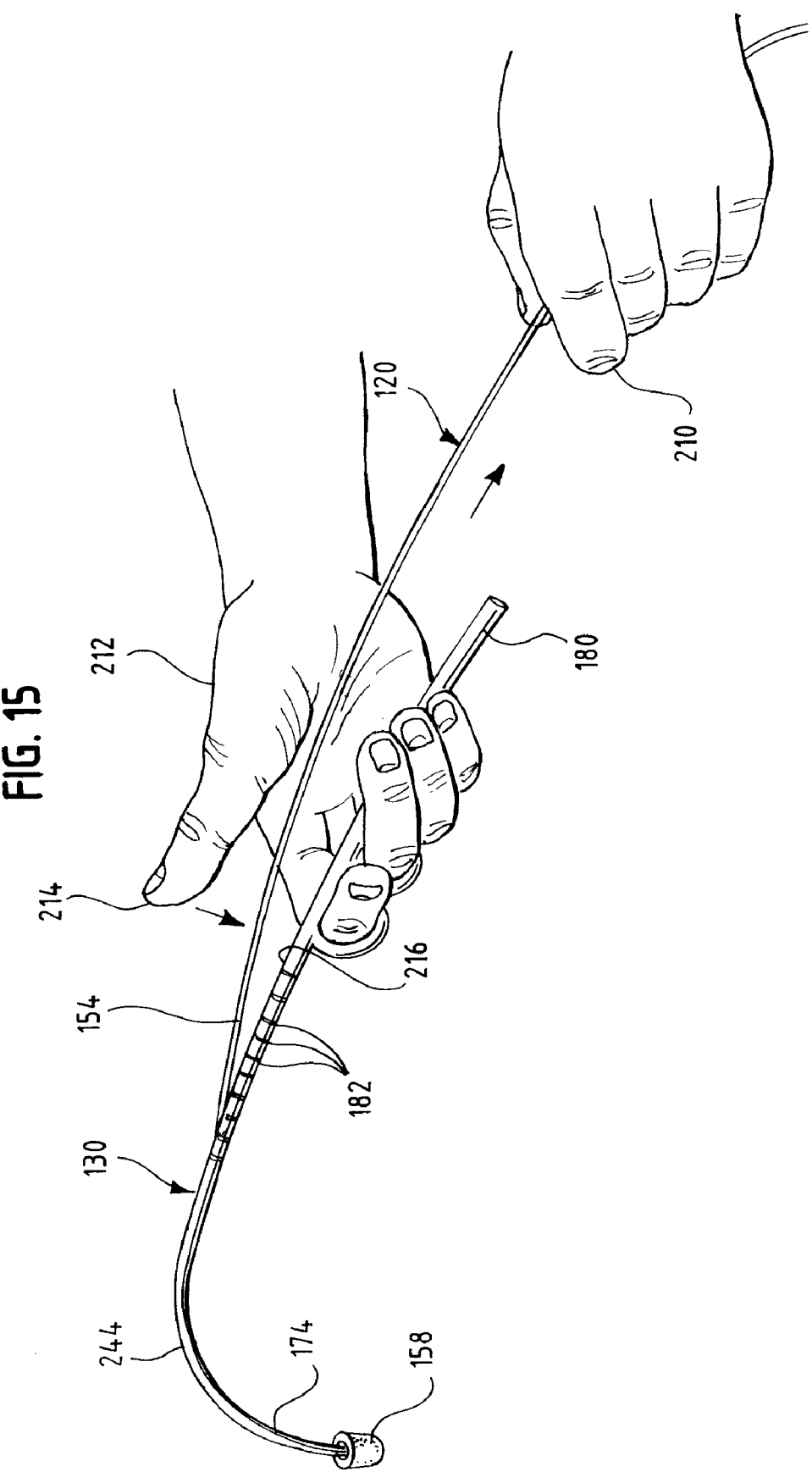

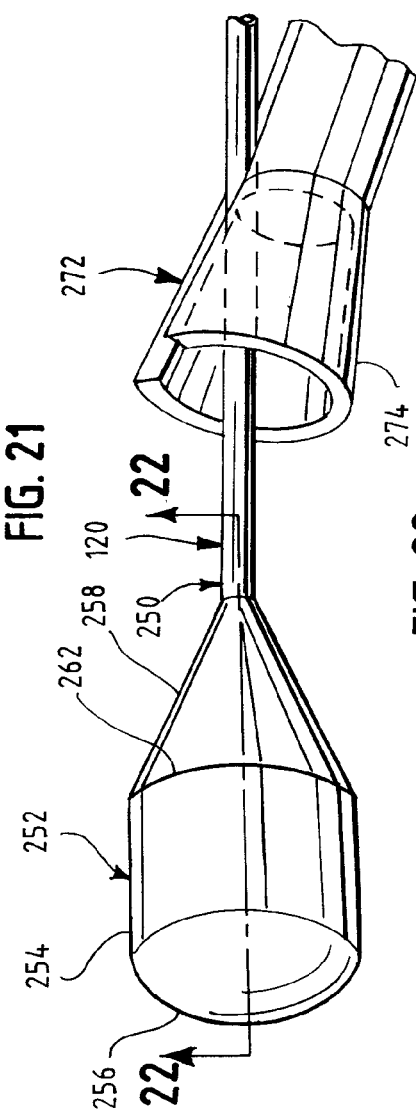
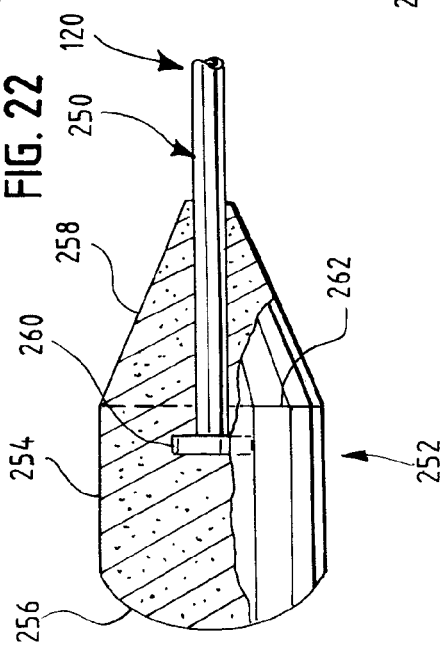
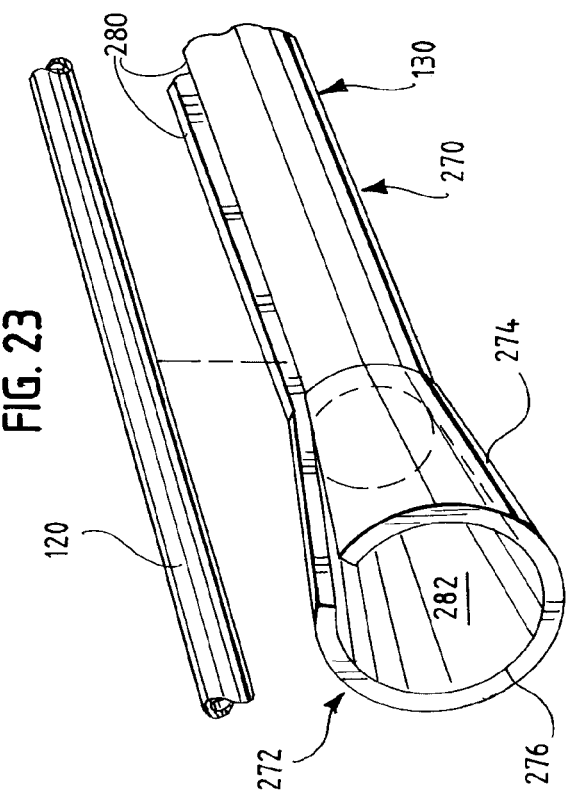

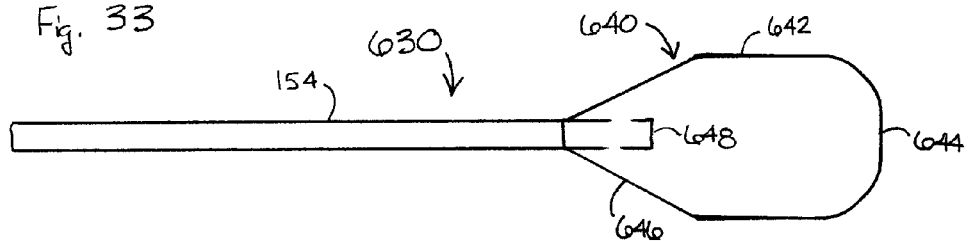
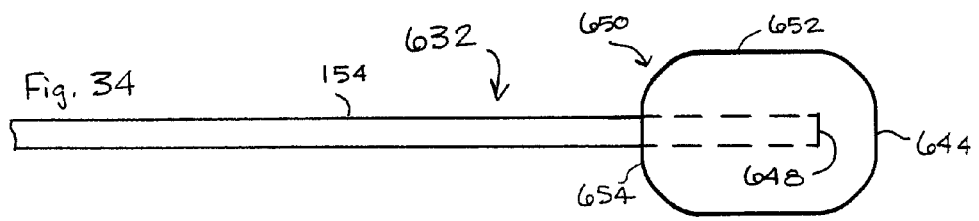
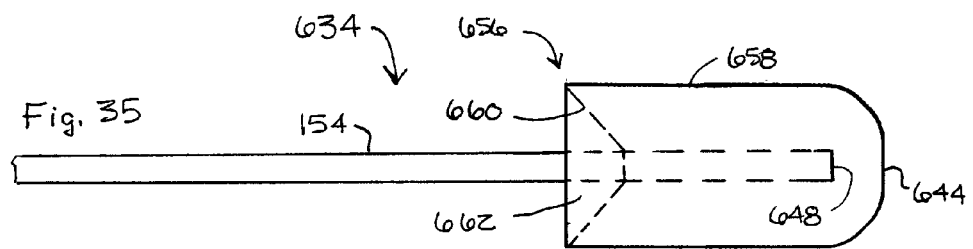
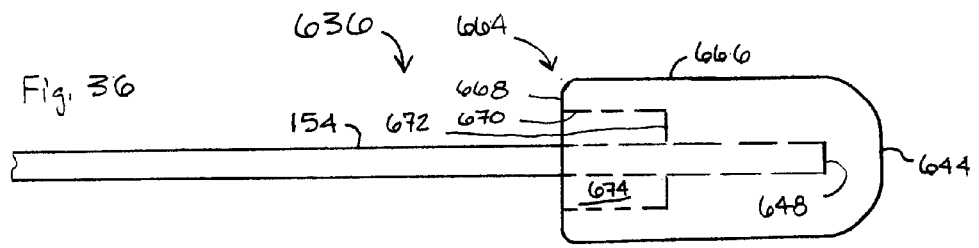
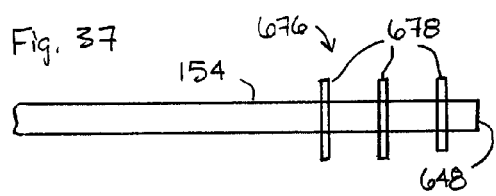
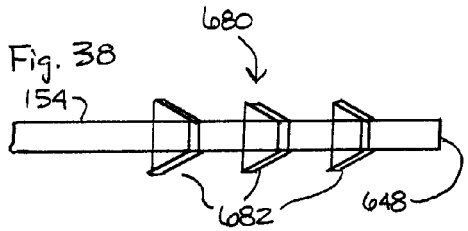

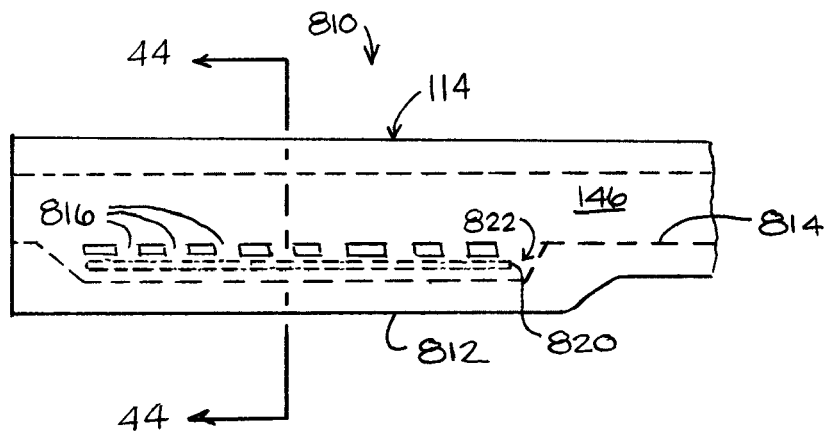
Fig 43
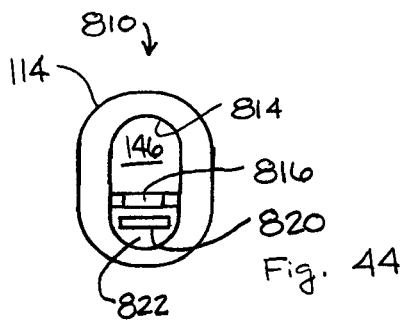
Fig. 44
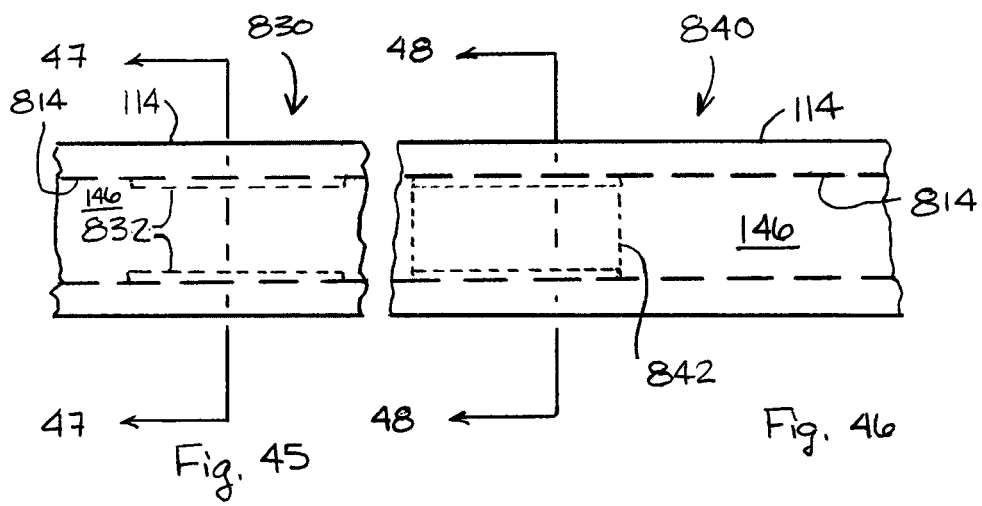
Fig. 45
Fig. 46
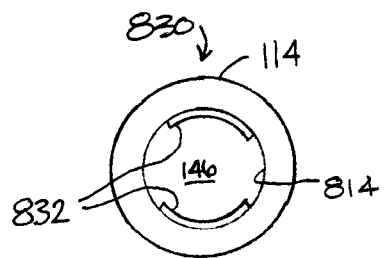
Fig. 47
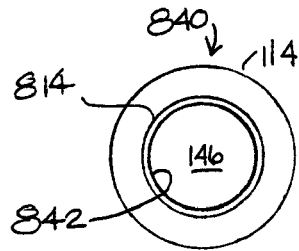
Fig. 48

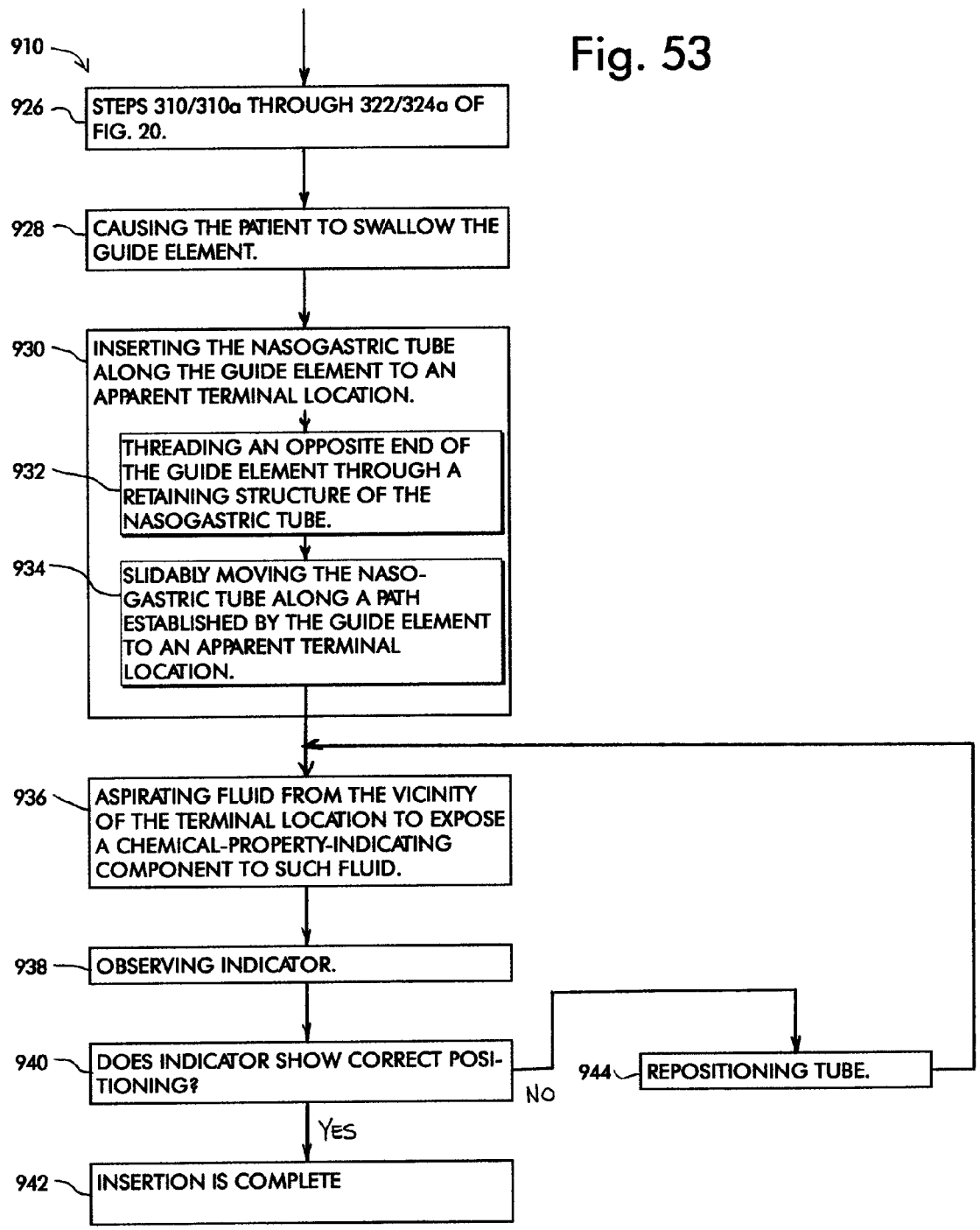

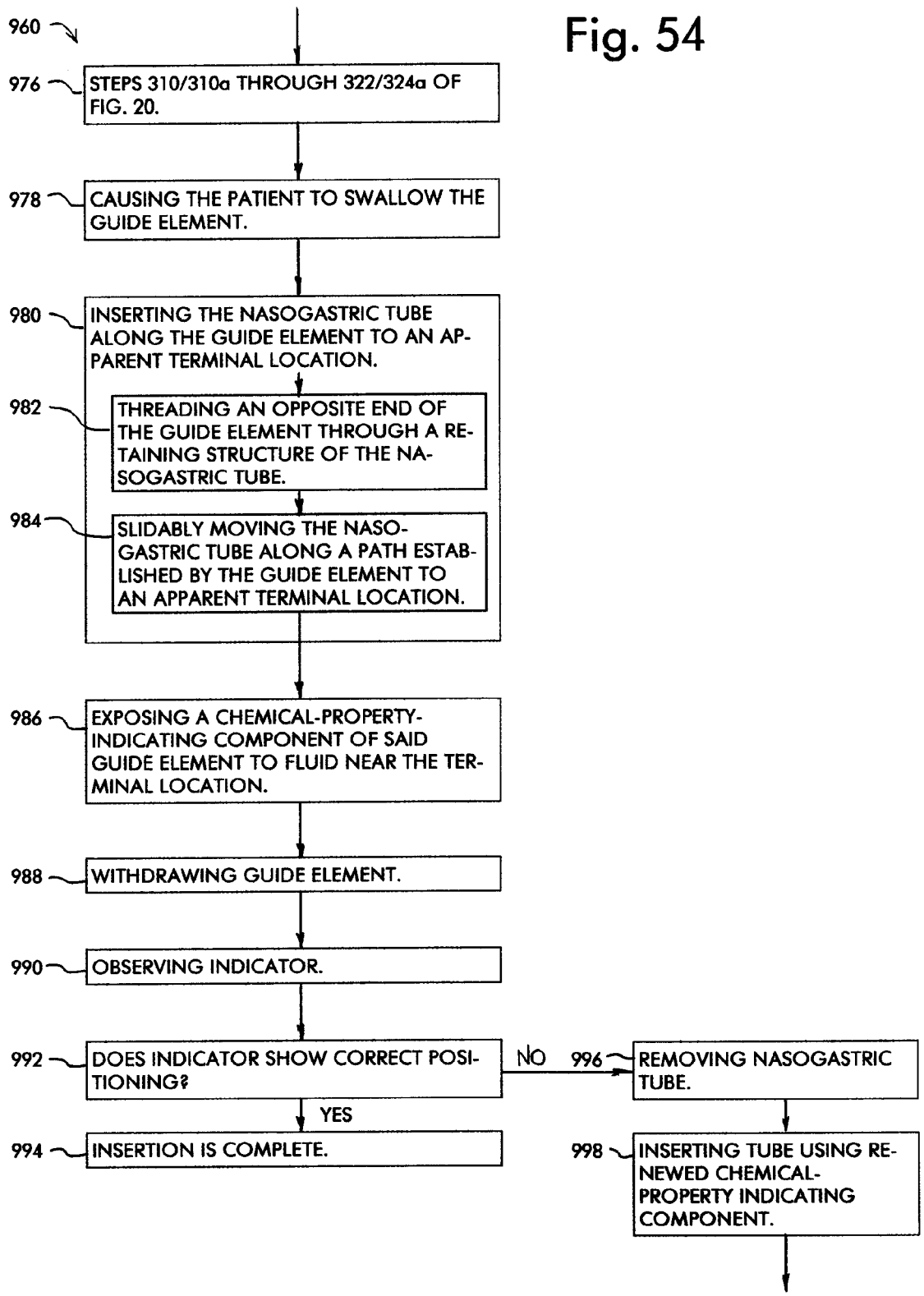

INSERTION SYSTEM AND METHODS FOR NASOGASTRIC TUBES

CROSS REFERENCE TO RELATED APPLICATIONS

This application is a Continuation-in-Part of application Ser. No. 11/548,086, filed 10 Oct. 2006, which is a Continuation-in-Part of application Ser. No. 11/347,481, filed 3 Feb. 2006, which claims the benefit under 35 U.S.C. Sec. 119(e) of application No. 60/650,806, filed 8 Feb. 2005.

FIELD OF THE INVENTION

This invention relates to nasogastric tubes, and more particularly to a system and method for inserting a nasogastric tube in a patient.

BACKGROUND OF THE INVENTION

A nasogastric tube is a generally flexible tube inserted through a patient's nasal passages to extend through the esophagus and into the stomach, for the purposes of allowing the introduction of fluids into the stomach, the removal of fluids from the stomach, or both. A nasogastric tube is often used in an emergency situation in an emergency room, trauma center, or immediate care facility. The nasogastric tube is usually inserted by or under the supervision of a physician. There are a number of situations in which the use of a nasogastric tube may be indicated, including, without limitation: upper gastrointestinal bleeding; a bowel obstruction or illeus; ingestion of a poison, contaminant, or drug of inappropriate kind or quantity (i.e., an "overdose"); or when whole bowel irrigation is needed.

Known nasogastric tubes are constructed of a generally flexible material and have one or more separate interior bores or lumina, each extending most of the length of the tube. Kim U.S. Pat. No. 3,999,554 discloses an exemplary nasogastric tube. Plural lumina allow multiple functions, such as the introduction of fluids, removal of fluids, and ventilation of the region around the end of the tube, to be performed simultaneously.

The construction of known nasogastric tubes varies, but in general, at one end intended for insertion into the patient, openings are provided to allow communication of fluids, possibly including gases, between the interior lumina and the region surrounding the end of the tube. At the opposite end of the nasogastric tube, separate sockets or tubes are provided for connection to various sources of fluids to be introduced into the patents stomach or to suction to remove fluids or gases from the patient's stomach.

Several significant disadvantages manifested by known nasogastric tubes arise during the process of inserting the nasogastric tube through the patient's nasal passages and into the stomach.

One disadvantage of known nasogastric tubes is the difficulty of safely inserting the nasogastric tube so that it does not incorrectly intubate the patient's trachea and lungs. Conventionally, the nasogastric tube is placed into the patient's nostril and pushed into the back of the oropharynx. The tube is typically lubricated at the tip. In some cases, the back of the oropharynx is numbed with a numbing spray. When the tube is in the oropharynx, the patient is asked to swallow the tube. The tube has some rigidity and cannot be independently swallowed by the patient. Instead, the person inserting the tube assists by pushing the tube into the esophagus and into the stomach while the patient is attempting to swallow.

Because the nasogastric tube is flexible and must undergo a significant bend in the oropharynx, it is impossible to precisely control the position of the end of the tube, and there is considerable risk that the tube will enter the trachea and eventually the lung, instead of the esophagus. Intubating the trachea and lung can have severe consequences, including death. Such intubation may cause damage to vocal cords and airway. It also may cause an extreme coughing and gag response in some patients. In some cases, the patient experiences such discomfort that the patient will not thereafter allow any further attempts at placing the nasogastric tube. In other cases, the patient may tolerate the nasogastric tube even after it has entered the lung, and may even be able to speak. This may cause the healthcare provider to erroneously believe the nasogastric tube has been properly placed in the stomach. If the nasogastric tube is incorrectly placed, and medication is improperly introduced into the lungs instead of the stomach, it could cause extreme morbidity or even death.

The epiglottis covers the trachea during the act of swallowing. The risk of intubating the trachea can be minimized by pushing the tube into the esophagus while the patient is attempting to swallow and entrance to the trachea is blocked by the epiglottis. However, this requires precise timing on the part of the medical professional who is inserting the tube. A further problem is that some patients cannot attempt to swallow because the tube activates their gag reflex. Although the tube is generally flexible, it is rigid compared to tissues of the oropharynx and esophagus, and even when a numbing agent has been used, some patients will gag. Because they are unable to swallow, the epiglottis does not cover the trachea and the nasogastric tube may intubate the trachea and lungs.

Another disadvantage of known nasogastric tubes is that pushing the hard tip of the nasogastric tube through the nasal passage and sinus often causes pain, bleeding, and significant trauma to the nasal cavity. The tube may abrade or irritate the tissues it encounters, particularly where it must bend downward toward the esophagus. In addition, the entire process can cause significant discomfort to the patient.

A further disadvantage of known nasogastric tubes is that it is difficult to verify that a nasogastric tube has been correctly placed in the patient's stomach without additional equipment, personnel, and effort. It is known to employ a radiopaque tracer wire or similar component in the nasogastric tube. Correct insertion can then be verified using conventional radiography or fluoroscopy. However, either of these procedures involves additional time, radiography equipment, technical personnel, and a significant cost.

Other workers in this field have sought to remedy some of these disadvantages. Knott U.S. Pat. No. 5,690,620 discloses an anatomically conforming nasogastric tube having a normally-curved or normally-bent leading end and an additional bend near the leading end. The bent portion of the nasogastric tube is intended to conform to the shape of the soft palate, thereby applying a reduced pressure against the posterior nasopharynx. Knott further discloses a method of inserting the nasogastric tube which involves rotating the tube to bias the bent leading end of the tube in various desired directions so as to avoid obstructions, reliably enter the esophagus, or bias the tip in a particular position with respect to the stomach outlet. However, Knott's apparatus and method do not assure that the leading end of the tube will not encounter, abrade, and irritate tissues during insertion. It also does not resolve the problem that the presence of the tube excites the patient's gag reflex. Moreover, rotating the trailing end of the tube does not ensure that the leading edge of the tube will identically rotate. Therefore, the difficulty of precisely positioning the leading end of the nasogastric tube remains. Thus, the Knott nasogastric tube does not satisfactorily resolve the problems of potentially intubating the trachea and lung, irritating or damaging the nasal cavity, and causing patient discomfort.

Peters U.S. Pat. No. 5,391,158 discloses a system for introducing a nasogastric tube into the stomach of a patient. The Peters system includes a digestible weight to be swallowed by the patient, and a digestible guide string having one end attached to the weight. The nasogastric tube is telescoped around the guide string; during the tube's insertion it follows the guide string into the patient's stomach. Peters discloses that the digestible weight is inserted through the patient's nostril to the nasopharynx.

However, Peters does not disclose how the weight is propelled to the nasopharynx, and it is believed this presents a significant difficulty in using the device. In addition, in many instances in which a nasogastric tube is needed, the patient's digestive system is not functioning properly. It is dangerous to assume that the "digestible" weight and guide string can actually be digested. The use of a "digestible" weight and string could even aggravate the patient's condition, and may cause other complications.

Moreover, the patient's digestion process, if it is operable at all, may take extensive time to digest the weight and string. Thus, the Peters nasogastric tube and insertion system also does not satisfactorily resolve the aforementioned disadvantages of known nasogastric tubes.

There has remained a need in the art for a nasogastric tube which can be safely inserted into the patient, which minimizes risk of intubating the trachea and lungs, which avoids damage to the oropharynx, the esophagus, and other tissues, and which minimizes patient discomfort during insertion.

OBJECT AND SUMMARY OF THE INVENTION

It is therefore an object of the present invention to minimize the aforementioned disadvantages of known nasogastric tubes.

A nasogastric tube insertion system constructed according to an aspect of the present invention includes an inserter element, a guide element, and a nasogastric tube.

The function of the inserter element is to aid in the initial placement of a portion of the guide element in the patient's oropharynx. The inserter element is constructed as a generally thin, longitudinal member having predominantly straight main body section and a curved insertion section.

A handle attached to and extending downward from the main body allows the inserter to be readily grasped and controlled by a user. The insertion section has one or more curved portions such that it generally conforms to the anatomy of a typical patient's nasal passages and oropharynx; the curved portions may have a total curvature in the range of approximately 70 to 100 degrees of arc in the direction of the handle. A section extending rearward of the main body section improves stability during handling of the device. The inserter element includes markings to allow the user to readily ascertain when a predetermined insertion depth has been reached. The tip of the insertion section may have a stepped portion of reduced thickness for loosely engaging the swallowable weight of the guide element.

Alternatively, the tip of the insertion section may have a conical-concave shape for receiving and loosely engaging a portion of the swallowable weight.

The function of the guide element is to establish a desired path for passage of nasogastric tube through the patient's nasal passages, the oropharynx, the esophagus, and the stomach, and to guide the nasogastric tube along that path during the tube's insertion. The guide element is constructed as a generally longitudinal thin cord or line having a leading section of sufficient flexibility to be easily inserted into and swallowed by the patient, and a trailing section of sufficient rigidity to guide the nasogastric tube as the tube is inserted. The trailing section also functions as a tether. A swallowable weight is attached to the leading section. The longitudinal portion of the guide element may be constructed as a unitary or monofilament line or piece, but may also be constructed as a string or cord, or a similar form of stranded or woven multifilament line. The swallowable weight may be constructed of a resilient, spongiform outer shell, with an interior structure, such as a cup, or anchor, for affixing the shell to the longitudinal portion of the guide element. The outer shell may be absorbent, in order to absorb a numbing agent or a vasoconstricting agent, and may, for example, be constructed from an open-cell foam.

The nasogastric tube is constructed as a generally slender tube having one or more interior bores or lumina extending along the length of tube for conducting fluids or gases between the patient's stomach and external sources, receptacles, or the atmosphere. The nasogastric tube has a leading end intended for insertion into the patient. A guide element retaining structure is provided near the leading end of the tube. The retaining structure has an eye or lumen for accepting the guide element and is arranged to allow the retaining structure, and the nasogastric tube in general, to slide along the guide element. The leading end of the nasogastric tube has one or more openings coupling the interior bores or lumina to the outside. The proximal end of the nasogastric tube also includes openings into the interior bores or lumina. Alternatively, the proximal end of the nasogastric tube may break out into one or more separate connection tubes coupled to the interior bores or lumina. The openings and connection tubes accommodate connection to fluid sources, vacuum "supplies," or the atmosphere, such that fluids and medications can be introduced into or removed from the patient's stomach, and may also allow gasses to be vented.

According to another aspect of the invention, a method for inserting a nasogastric tube includes the steps of attaching the swallowable weight to the tip of the inserter element; optionally applying a numbing or vasoconstricting agent to the swallowable weight; inserting the inserter element through the patient's nasal passages for a predetermined distance, thereby placing the swallowable weight in an expected location, past the narrow nasal passages, which may be the patient's nasopharynx or possibly the oropharynx; releasing the weight from the tip of the inserter element; optionally extending the guide element a further distance into the nasal passage or oropharynx; having the patient swallow the weight, thereby placing the weight into the patient's stomach; optionally threading the free end of the guide element through an opening of the guide element retaining structure of the nasogastric tube; and inserting the nasogastric tube through the patient's nasal passages and into the patient's stomach along the guide element, thereby following the path established by the guide element. The inserter element may be removed after the weight has been positioned in the oropharynx. Alternatively, the inserter element may be removed at an earlier stage when the weight is in the nasopharynx or nasal turbinates. In the latter case, the weight may then be advanced using gentle longitudinal pressure on the guide element. The weight and guide element may remain in the patient's stomach until they and the nasogastric tube are withdrawn together. Alternatively, the guide element, including the weight, may be withdrawn soon after insertion of the nasogastric tube is complete. The steps of attaching the swallowable weight to the tip of the inserter element and threading the free end of the guide element through an opening of the guide element retaining structure may be performed as a part of the process of manufacturing the nasogastric tube insertion system rather than as part of the insertion process.

According to a further aspect of the present invention, nasogastric tubes of various designs and functions may be inserted using the inserter element, the guide element, and the associated methods described earlier. For example, a nasogastric tube adapted for use as a feeding tube may be advantageously used with the aforementioned elements. A nasogastric feeding tube is generally similar to the earlier-described nasogastric tube, but has several differences to accommodate its use as a feeding tube. Because feeding tubes are often left in position in the patient for an extended period, and the tubes are typically used to deliver fluid under slight positive pressure but are not subject to suction, the main tubular section is usually constructed of very flexible material having thin walls to minimize damage and discomfort to the patient. Typical feeding tubes have a single lumen, but some feeding tubes have more lumina and some feeding tubes are adapted to permit suction to be applied. The proximal end includes one or more ports leading to the lumen for introducing nutritional, hydration, tube-flushing, and drug products in fluid form.

The distal end has a terminating chamber in communication with the lumen; the chamber has one or more exit "windows" or openings to permit fluid to leave the chamber. A removable stylet may be provided to afford sufficient stiffness to allow the device to be inserted. The distal end may also have one or more weights to facilitate insertion and to maintain the position of the end thereafter. A guide element retaining structure is provided near the leading end of the feeding tube. The retaining structure has an eye or lumen for accepting the guide element and is arranged to allow the retaining structure, and the feeding tube in general, to slide along the guide element.

The feeding tube may be inserted using a method similar to that described earlier for other nasogastric tubes, but preferably incorporates additional steps of verifying correct positioning of the distal end of the tube.

According to a further aspect of the invention, the guide element may be a flexible sac or balloon which is normally inflated and is deflated after the nasogastric tube has been inserted. After the weight is deflated, the guide element may be withdrawn from the patient while the nasogastric tube remains in place.

According to a further aspect of the invention, the guide element swallowable weight may be constructed from an ablatable material (e.g., a material that dissolves, disintegrates, melts, sublimates, decomposes, falls away, erodes, softens to allow reshaping with minimal force, or the like) when exposed to stomach fluids or to the temperature present in the body. When the weight is ablated from the guide element, the guide element may be withdrawn from the patient while the nasogastric tube remains in place. The weight may be formed from a variety of materials and may be constructed using any appropriate methods, including molding, casting, or compressing the material about the end of the guide element. The guide element may have retaining structures near its end to retain or capture the weight before its ablation.

According to a further aspect of the invention, chemical-property indicating media may be provided in the nasogastric tube or on the guide element to allow the user to verify correct placement of the nasogastric tube in the patient's stomach. The indicating media may be incorporated into a visible portion of the nasogastric tube near its proximal end. Fluids in the vicinity of the distal end of the nasogastric tube may be aspirated into contact with the indicating media. Stomach fluids generally exhibit a pH in a known range. Body fluids found in locations other than the stomach exhibit a pH outside this range. By employing a medium that indicates when pH of the aspirated fluid is within the expected range, the medium provides a visual indication of whether the fluid has been aspirated from the stomach or elsewhere. The user can employ this indication to verify that the nasogastric tube has been correctly inserted. Different, visually or spatially distinct indicating media may be used to indicate different chemical properties or values thereof. The media may be formed in characters, symbols, or glyphs that correspond to the properties or values indicated. Chemical-property indicating media may also be applied to the leading section of the guide element. The leading section of the guide element is colocated with the distal end of the nasogastric tube, and so the indicating media also indicates the properties of the fluid in the vicinity of the distal end of the tube. The indicator is visible and may be inspected after the guide element is withdrawn from the body. If an ablative swallowable weight is provided as part of the guide element, the indicating media may be applied to the portion of the guide element covered by the weight. In that case, the indicating media is not exposed to stomach fluids until the weight has been ablated.

BRIEF DESCRIPTION OF THE DRAWINGS

These and other features of this invention will be best understood by reference to the following detailed description of a preferred embodiment of the invention, taken in conjunction with the accompanying drawings, in which:

FIG. 11 is a side view of an inserter element 130 of the nasogastric tube insertion system 100 of FIG. 1;

FIG. 12 is an enlarged side view of the insertion section 174 of inserter element 130 of FIGS. 1 and 11 and the leading section 154 of guide element 120 of FIGS. 1-4 showing the insertion section 174 about to be attached to the guide element 120;

FIG. 13 is an enlarged perspective view of the tip 186 of insertion section 174 of inserter element 130 of FIGS. 1, 11, and 12 and a portion of the leading section 154 of guide element 120 of FIGS. 1-4;

FIG. 14 is a side view showing the guide element 120 of FIGS. 1-4 attached to the inserter element 130 of FIGS. 1, 11, and 12, and depicting a stage in an exemplary method of inserting the nasogastric tube insertion system 100 in which the swallowable weight 158 is held on the tip 186 of inserter element 130 by tension on the guide element 120 provided by the user;

FIG. 15 is a side view showing the guide element 120 of FIGS. 1-4 attached to the inserter element 130 of FIGS. 1, 11, and 12, and depicting another stage in the method of inserting the nasogastric tube insertion system 100 in which the swallowable weight 158 is held on the tip 186 of inserter element 130 by tension on the guide element 120 provided by the user;

FIG. 21 is an enlarged side view of an alternative embodiment 270 of the insertion section of inserter element 130 of FIGS. 1 and 11 and an alternative leading section 250 of guide element 120 of FIGS. 1-2, showing the alternative insertion section 270 about to be attached to the guide element 120;

FIG. 22 is an enlarged cross-section view of an alternative embodiment 250 of the leading section of the guide element 120 of FIG. 21, taken along the section line 22-22 thereof;

FIG. 23 is an enlarged perspective view of the tip 272 of alternative insertion section 270 of inserter element 130 of FIGS. 1 and 21 and a portion of the alternative leading section 250 of guide element 120 of FIG. 22;

FIG. 33 is a side view showing the leading section of an alternate embodiment of a guide element with a weight element thereof having a first example configuration;

FIG. 34 is a side view showing the leading section of an alternate embodiment of a guide element with a weight element thereof having a second example configuration;

FIG. 35 is a side view showing the leading section of an alternate embodiment of a guide element with a weight element thereof having a third example configuration;

FIG. 36 is a side view showing the leading section of an alternate embodiment of a guide element with a weight element thereof having a fourth example configuration;

FIG. 37 is a side view showing the leading section of an alternate embodiment of a guide element before the weight element thereof is installed, depicting a first example configuration of members for retaining the weight element;

FIG. 38 is a side view showing the leading section of an alternate embodiment of a guide element before the weight element thereof is installed, depicting a second example configuration of members for retaining the weight element;

FIG. 43 is a side view of the proximal end section of an alternate embodiment of a nasogastric tube showing a chemical-property indicating element thereof;

FIG. 44 is a cross section view of the alternate embodiment of the nasogastric tube of FIG. 43, taken along the section lines 44-44 of FIG. 43;

FIG. 45 is a side view of the proximal end section of a further alternate embodiment of a nasogastric tube showing a chemical-property indicating medium thereof in a first example configuration;

FIG. 46 is a side view of the proximal end section of a further alternate embodiment of a nasogastric tube showing a chemical-property indicating medium thereof in a second example configuration;

FIG. 47 is a cross section view of the alternate embodiment of the nasogastric tube of FIG. 45, taken along the section lines 47-47 of FIG. 45;

FIG. 48 is a cross section view of the alternate embodiment of the nasogastric tube of FIG. 46, taken along the section lines 47-47 of FIG. 45;

FIG. 53 is a flow diagram showing an example method according to an aspect of the invention for determining correct insertion of a nasogastric tube by exposing a chemical property indicator such as those shown in FIGS. 43-50; and FIG. 54 is a flow diagram showing an example method according to an aspect of the invention for determining correct insertion of a nasogastric tube by exposing a chemical property indicator such as those shown in FIGS. 51-52.

DETAILED DESCRIPTION OF THE PREFERRED EMBODIMENT

A preferred embodiment of nasogastric tube insertion system 100 constructed according to the present invention is shown generally in FIGS. 1-20. The nasogastric tube insertion system 100 is intended for use with a patient who is conscious, alert, and able to swallow.

Figure 1:
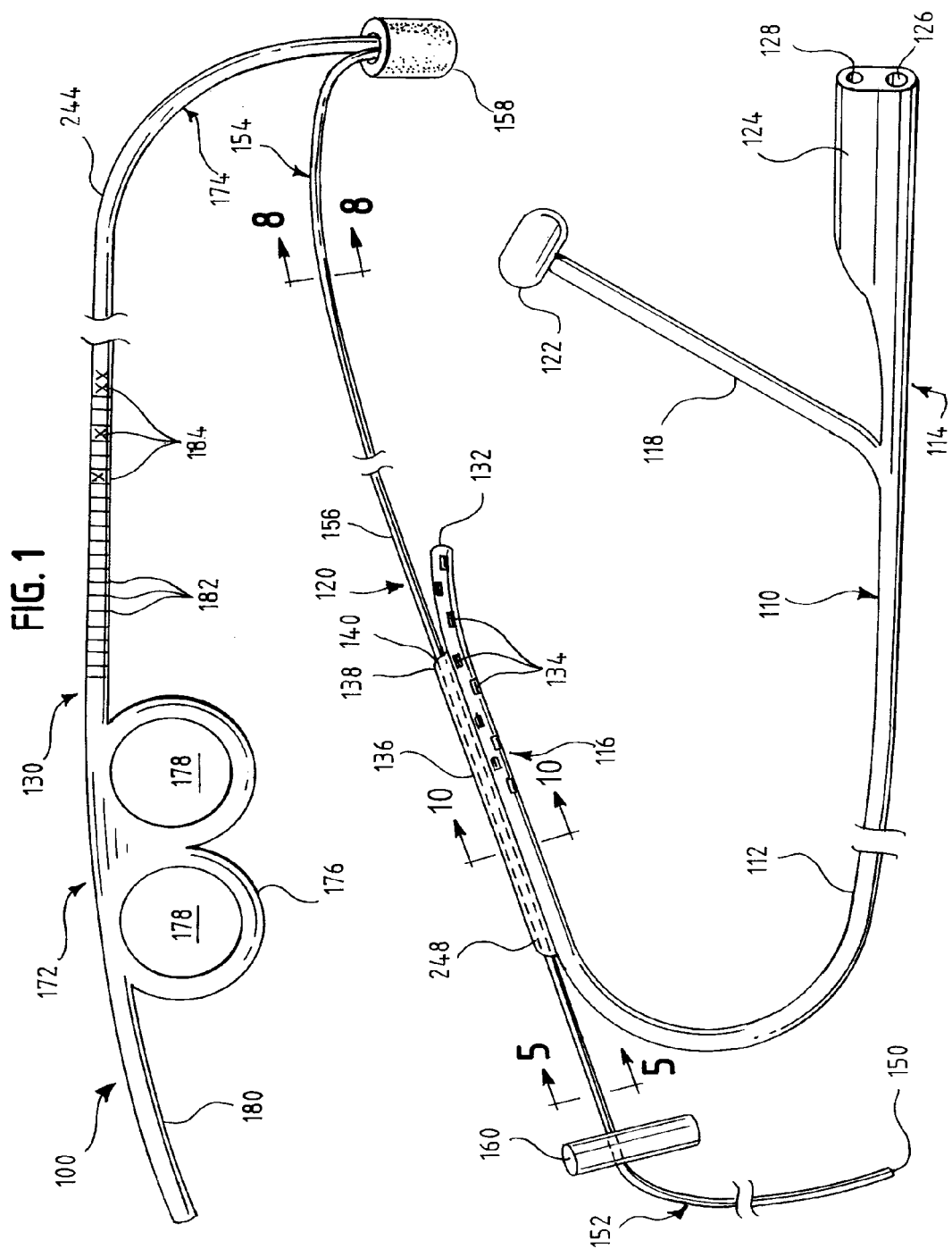
FIG. 1 is an overall side view of an exemplary embodiment of a nasogastric tube insertion system 100 constructed according to an aspect of the present invention.

As best seen in FIG. 1, the nasogastric tube insertion system 100 comprises a nasogastric tube 110, a guide element 120, and an inserter element 130. The function of the inserter element 130 is to aid in the initial placement of a portion of the guide element 120 in the patient's oropharynx.

The function of the guide element 120 is to establish a desired path for passage of nasogastric tube 110 through the patient's nasal passages, the oropharynx, the esophagus, and the stomach, and to guide the nasogastric tube 110 along that path during the tube's insertion.

FIGS. 24-28, discussed further in greater detail, depict alternate embodiments of a nasogastric tube which may be used in conjunction with the guide element 120 and inserter elements of the present invention. One of skill in the art will appreciate that although several embodiments of nasogastric tubes are described herein as examples by which aspects of the present invention may be implemented, the inserter element, guide element, and associated methods could be used for other types of nasogastric tubes and for other similarly configured objects which are desired to be inserted through the patients nostrils.

FIG. 1 depicts a configuration in which the nasogastric tube 110, guide element 120, and inserter element 130 are simultaneously connected to or engaged with one another, and a commercial embodiment of the nasogastric tube insertion system 100 could be so constructed. However, it will be appreciated that is not necessary that these components ever actually be arranged in that configuration. It is sufficient that the guide element 120 be attached to the inserter element 130 during the insertion of a portion of the guide element into the patient's oropharynx. In a subsequent step, it is sufficient that the guide element 120 be partially enveloped by or threaded through a portion of the nasogastric tube 110 during the insertion of the tube 110 in order that the tube 110 follow the path established by the guide element 120.

As best seen in FIGS. 1 and 11, the inserter element 130 is constructed as a generally thin, longitudinal member having predominantly straight, slender, and elongate main body section 172 and a curved insertion section 174 which is adapted to engage an end of guide element 120 to enable insertion of the guide element into the patient's nasal passage or oropharynx. The insertion section 174 shown and described in connection with these figures is a first exemplary embodiment constructed according to an aspect of the present invention. An alternative embodiment 270 of the insertion section, adapted for use with an alternative embodiment 250 of the leading section of guide element 120, is shown in FIGS. 21-22 and described further in greater detail.

The inserter element 130 preferably comprises a handle 176 to allow the inserter element 130 to be readily grasped and controlled by a user. An exemplary configuration for handle 176 is shown in FIGS. 1 and 11, in which the handle is formed as two loops of structural material attached to and extending downward from the main body 172. The loops form handle openings 178, which may, for example, receive the user's index and middle fingers and allow the inserter element 130 to be grasped. A stabilizing extension 180 extending from the main body section rearward of the handle 176 improves stability during handling of the inserter element 130. Other handle configurations could also be used.

The main body 172 of the inserter element 130 may be constructed of any suitable material having sufficient thickness and strength to be handled and to support the modest weight of the insertion section 174 and a portion of the guide element 120 which is attached thereto during the insertion process. For example, the insertion section 174 may be constructed of semi-flexible, biologically inert material, such as clear poly-vinyl chloride. Other materials could also be used. The cross section and exact dimensions of the main body 172 are non-critical but may be selected to optimize cost, user comfort, and compatibility with the insertion section 174.

The insertion section 174 preferably has one or more curved portions such that it generally conforms to the anatomy of a typical patient's nasal passages and oropharynx. The curved portions may cumulatively provide curvature in the range of approximately 70 to 100 degrees of arc in the direction of the handle 176.

The insertion section 174 is preferably constructed of a flexible, biocompatible material, providing sufficient stiffness to support the swallowable weight 158 of guide element 120, but also providing enough flexibility to deform as needed, during insertion of the insertion section 174 into the patient's nasal passages, to pass any obstacles encountered without injury or abrasion. For example, the insertion section 174 may be constructed of semi-flexible, biologically inert material, such as clear poly-vinyl chloride. Other materials could also be used. The insertion section 174 may have any suitable cross section, including without limitation a generally circular, semi-circular, oval, oblong, or rectangular cross section. The cross-section of insertion section 174 may permit more flexibility in the direction of curvature than in directions perpendicular thereto. As discussed further in greater detail, the insertion section 174 preferably has a groove or channel 194 (FIG. 13) along at least a portion of its dorsal surface to receive a portion of the guide element 120. The insertion section 174 is preferably free of sharp exterior edges or other structures that may cause injury or abrasion of tissues in the nasal passages.

The exact dimensions of the insertion section 174 are non-critical, but preferably are selected as appropriate for the material used, to provide a desired amount of stiffness and flexibility, and to allow the inserter to easily enter and pass through the nasal passages of a patient. The insertion section 174 should be long enough that, when inserted, the tip 186 can reach into the patient's oropharynx without requiring the handle 176 to impinge on the patient's face. It is believed that an insertion section 174 having a width less than or equal to about 0.75 cm, a thickness less than or equal to about 0.5 cm, and a length of approximately 25 cm or more, would be appropriate for use with an adult patient of typical size. Smaller dimensions may be needed for use with smaller patients, including children and infants. In addition, the dimensions could be varied to achieve desired variations in stiffness or other mechanical parameters. For example, if increased flexibility is desired toward the end of the insertion section 174, the thickness or width may be gradually reduced in that section. The main body 172 and insertion section 174 may be separately constructed and later assembled to form a unit. Alternately, the main body 172 and insertion section 174 may be constructed as a single unit, and there may be no visible structural characteristics that signal when one ends and the other begins.

The inserter element 130 preferably has measurement lines 182 or other suitable indicia to allow the user to readily ascertain when the inserter has been inserted to a predetermined insertion depth, corresponding to the placement of the end of the insertion section 174, and the swallowable weight 158 attached thereto, in a desirable location in the patient's oropharynx.

For most patients, an optimal predetermined insertion depth may be found by measuring the distance between the patient's earlobe and the tip of the patient's nose. The inserter element 130 may also have measurement legend indicia 184 specifying units of measurement or other related information associated with measurement lines 182. However, the user may perform the distance measurement using the inserter element 130 itself, e.g., by marking the distance on the measurement lines 182.

Although it is normally expected that the desired inserter-assisted placement of the swallowable weight 158 be into the patient's oropharynx, it may be preferable in some situations to use the inserter element 130 to place the swallowable weight 158 only part way into the nasal passages. In those situations, the swallowable weight 158 would then be released from the inserter element 130, and the user would advance the guide element 120 into the oropharynx by applying longitudinal pressure, relying on the stiffness of the guide element to assist placement. A shorter inserter element 130 could be used for such situations, and the desired insertion distance could be measured using different benchmarks on the patient's face or body.

As best seen in FIG. 13, the insertion section 174 preferably has walls 196 forming a groove or channel 194 along at least a portion of its dorsal surface 244 to receive the guide element 120. An alternative embodiment 270 of the insertion section is shown in FIGS. 21-23 and described further in greater detail. Once the swallowable weight 158 of the guide element 120 is placed on the end of the inserter element 130, in order to retain the swallowable weight 158 in position, the user must apply light tension on the guide element 120. The channel 194 is adapted to retain the guide element 120 along the top surface of the inserter element 130 while tension is applied. This avoids undesirably deforming the insertion section 174 and prevents the guide element 120 from taking on a "bow string" configuration, which would interfere with the insertion process.

Although channel 194 is depicted in FIG. 13 as a generally U-shaped channel of considerable depth, other configurations could also be used provided they retain the guide element 120 along the dorsal surface 244 of the inserter element 130 while light tension is applied to the guide element 120. For example, the depth of the channel could be significantly less than depicted. For another example, the channel-forming walls 196 could be formed as two or more longitudinal ridges on the dorsal surface of the guide element 120, which might otherwise be flat. The ridges could be of any height that satisfactorily retains the guide element 120 while light tension is applied. The term "dorsal" is used here to refer to the upper surface 244 of the inserter element 130, as shown in FIGS. 1 and 11, without respect to the orientation in which the inserter element 130 is held.

As best seen in FIGS. 11-13, the tip 186 of the insertion section 174 has a stepped engagement section 188 of reduced thickness for loosely engaging the swallowable weight 158 of the guide element 120. As mentioned above, once the swallowable weight 158 is placed onto the tip 186 of the insertion section 174, the tip is preferably held in place by light tension on guide element 120. The loose engagement preferably allows the swallowable weight 158 to be released from the tip 186 by releasing tension on the guide element 120, allowing the swallowable weight 158 to fall away. FIGS. 12 and 13 depict the tip 186 and stepped engagement section 188 in alternate configurations. FIGS. 21 and 23 depict an alternative embodiment 270 of the insertion section and will be discussed further in greater detail.

In FIG. 12, there is shown a first embodiment in which the tip 186 has an angular chamfered section 190 adapted to engage a mating receptacle 168 of the swallowable weight 158 of the guide element 120. Substantially vertical step walls mark the boundary between the full-thickness portion of the insertion section 174 and the stepped engagement section 188. The stepped engagement section 188 extends a short distance from the step walls 198 to the tip 186. The leading section 154 of guide element 120 is retained in channel 194 (FIG. 13) when the swallowable weight 158 is placed on tip 186 and light tension is applied to guide element 120.

In FIG. 13, there is shown a second embodiment in which the tip 186 has a substantially vertical wall section 192 instead of the angular chamfered section 190 of FIG. 12. Angular step walls 242 mark the boundary between the full-thickness portion of the insertion section 174 and the stepped engagement section 188. The stepped engagement section 188 extends a short distance from the step walls 242 to the tip 186. The leading section 154 (FIG. 12) of guide element 120 is retained in channel 194 when light tension is applied to guide element 120.

Figure 2:
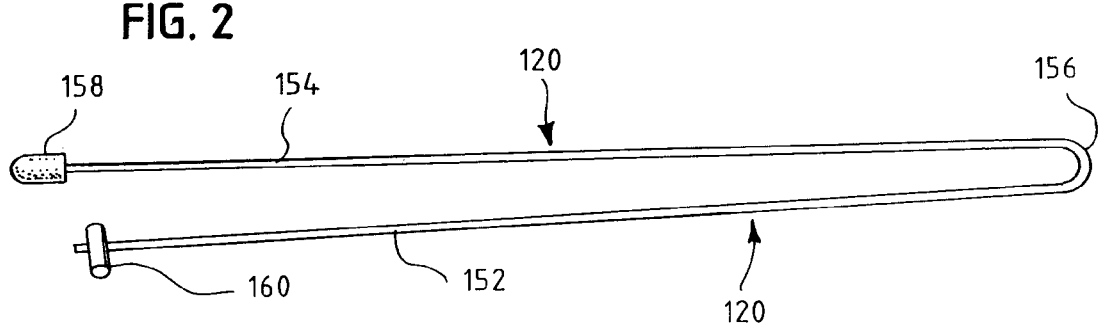
FIG. 2 is a side view of a guide element 120 of the nasogastric tube insertion system 100 of FIG. 1, showing the guide element in another configuration.

As best seen in FIGS. 1-2, the guide element 120 is constructed as a thin, elongate or generally longitudinal element, which may be a cord or line, having a leading section 154 having sufficient flexibility to be easily inserted into and swallowed by the patient, and trailing section 152 having sufficient rigidity to guide the nasogastric tube 110 as the tube is inserted. The trailing section also functions as a tether. A swallowable weight 158 is attached to the leading section 154. A transition 156 joins the trailing section 152 and leading section 154. A stopper 160 may be provided near the end 150 of guide element 120 opposite the swallowable weight 158 to prevent the end from being swallowed by the patient. Alternatively, the trailing section 152 could be extremely long, such that it cannot be swallowed. An alternative embodiment 250 of the leading section of guide element 120 is shown in FIGS. 21-22 and described further in greater detail.

The trailing section 152 of the guide element 120 may be constructed of any suitable material having sufficient thickness, flexibility and strength to be handled and to reliably avoid breakage. The trailing section 152 is preferably be rigid enough to navigate over the trachea and into the esophagus, but flexible enough to be readily swallowed. For example, the trailing section 152 may be constructed of a silicone elastomer or of a polymer in the nylon family. Other highly-flexible, biologically inert materials could also be used.

The leading section 154 is preferably constructed of any suitable biocompatible material, having sufficient thickness, flexibility and strength to be handled and to reliably avoid breakage. The leading section 154 is preferably flexible enough to be very easily swallowed. Because the leading section 154 will be swallowed and will be subject to digestive acids and enzymes for some period, the material from which the leading section 154 is constructed is preferably highly resistant to attack from such agents. For example, the leading section 154 may be constructed of a silicone elastomer or of a polymer in the nylon family. Other highly-flexible, biologically inert materials could also be used. Preferably, the trailing section 152 is free of sharp edges and has suitable outer surface features and finish to avoid injury or abrasion of tissues when the leading section 154 is swallowed and removed. In some situations, it may be desirable to use the inserter element 130 to assist the insertion of the leading section 154 of guide element 120 only part way into the patient's nasal passages, and then to use longitudinal pressure on the guide element 120 to further advance the leading section 154 into the patient's oropharynx without the continued assistance of the inserter element 130.

In such situations, it is desirable that leading section 154 possess sufficient stiffness accommodate advancement of the leading section into the oropharynx, while retaining sufficient flexibility to avoid damaging tissues during insertion and removal.

Figure 5:
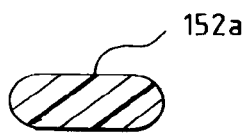
FIG. 5 is a cross-section view of the trailing section 152 of the guide element 120 of FIG. 1 taken along section line 5-5 thereof.
Figure 6:
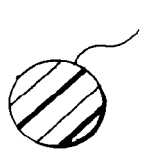
FIG. 6 is a cross-section view of an alternate embodiment of the trailing section 152 of the guide element 120 of FIG. 1 taken along section line 5-5 thereof.
Figure 7:
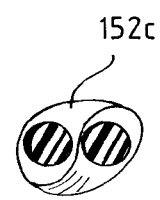
FIG. 7 is a cross-section view of another alternate embodiment of the trailing section 152 of the guide element 120 of FIG. 1 taken along section line 5-5 thereof.
Figure 8:
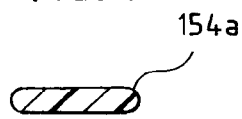
FIG. 8 is a cross-section view of the leading section 154 of the guide element 120 of FIG. 1 taken along section line 8-8 thereof.

As best seen in FIGS. 5-7 and 8-9, the longitudinal elements 152, 154 of the guide element 120 may be constructed as a unitary or monofilament line or piece, or as a string or cord, or similar form of stranded or woven multifilament line. FIGS. 5 and 8 depict in cross section a first exemplary embodiment of the guide element 120 in which the trailing section 152a is formed as an element of generally oval or oblong cross section, and the leading section 154a is also formed as an element of generally oval or oblong cross section of somewhat reduced size.

Figure 9:
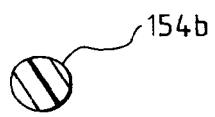
FIG. 9 is a cross-section view of an alternate embodiment of the leading section 154 of the guide element 120 of FIG. 1 taken along section line 8-8 thereof.

FIGS. 6 and 9 depict in cross section a second exemplary embodiment of the guide element 120 in which the trailing section 152b is formed as an element of generally circular cross section, and the leading section 154b is also formed as an element of generally circular cross section of somewhat reduced size. FIG. 7 depicts in cross section a third exemplary embodiment of the guide element 120 in which both the trailing and leading section 152c are formed as a twisted bifilar cord.

The elements may be formed by molding, extrusion, drawing, or any other suitable method of manufacture. These particular configurations are provided by way of example, not limitation, and it will be appreciated that other cross sections, number of filaments, stranding configurations, and the like could also be used, and that the configuration used for the leading section 154 may differ from that used for the trailing section 152.

The exact dimensions of the leading section 154 and the trailing section 152 of guide element 120 are non-critical but may be selected to optimize cost, compatibility with one another, and with a guide element retaining structure 136 of nasogastric tube 110 (FIGS. 1, 10), discussed further in greater detail. A leading section 154 having a width in the range of approximately 0.1-2.5 mm and a thickness in the range of approximately 0.1-2.5 mm, would be appropriate, but the necessary dimensions may vary depending on material choices, the flexibility or stiffness desired, and other factors. A trailing section 152 having a width in the range of approximately 0.1-3.5 mm, and a thickness in the range of approximately 0.1-3.5 mm would be appropriate, but the necessary dimensions may vary depending on material choices, the flexibility or stiffness desired, and other factors. The trailing section 152 and leading section 154 may be separately constructed and later assembled to form a unit. Alternately, the trailing section 152 and leading section 154 may be constructed as a single unit.

A transition area 156 designates the area at which trailing section 152 is joined to leading section 154. If these components are formed as an integrated unit of the same size and cross-section throughout, the transition area may not be apparent. If the trailing section 152 and leading section 154 are dissimilar, the leading section 154 is preferably long enough to allow the patient to swallow the swallowable weight 158 into the stomach without ingesting part of the trailing section 152. Also, the change from leading section 154 to the trailing section 152 may be gradual rather than abrupt.

Figure 3:
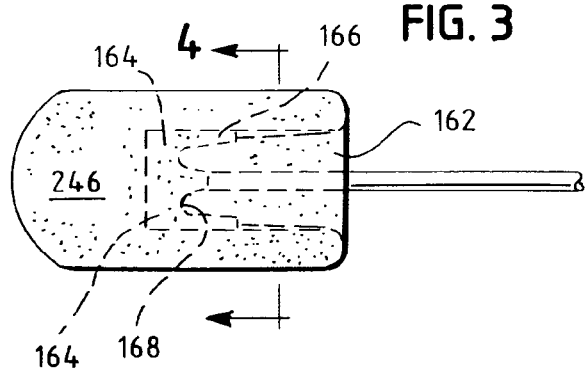
FIG. 3 is an enlarged side view of the leading section 154 of the guide element 120 of FIGS. 1-2.
Figure 4:
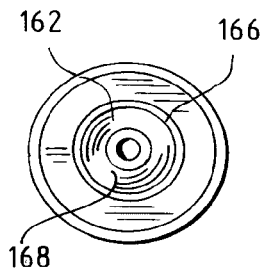
FIG. 4 is a partial cross-section view of the leading section 154 of the guide element 120 of FIGS. 1-3 taken along section line 4-4 of FIG. 3.

As best seen in FIGS. 3, 4, and 12, the swallowable weight 158 is attached to the leading section 154 of guide element 120. The swallowable weight 158 preferably comprises a resilient body 246 and an interior attachment structure 164 for affixing the shell to the leading section 154 of the guide element 120. An alternative embodiment 252 of the swallowable weight is shown in FIGS. 21 and 22, and described further in greater detail.

The body 246 is preferably soft and resilient so that it may be easily swallowed with minimal discomfort to the patient and so that it avoids abrading or irritating tissues when it is inserted through the patient's nasal passages into the oropharynx. The body 246 is preferably constructed from a flexible, absorbent, biocompatible material, which may, for example, be a spongiform material such as open-cell foam. Other materials could also be used. Because the body 246 will be swallowed and will be subject to digestive acids and enzymes for some period, the material from which the body 246 is constructed is preferably highly resistant to attack from such agents. Although the swallowable weight 158 is referred to as a weight, it need not be heavy or constructed of dense materials. It is sufficient that the weight be easily swallowed. The dimensions of the swallowable weight 158 are not critical, but the weight is preferably of a size that can be easily swallowed and can easily pass through the patient's nasal passages. A diameter in the range of approximately 0.4-1.25 cm, and a length in the range of approximately 0.7-1.7 cm are believed to be suitable for most adult patients. Other sizes could also be used; a smaller weight may be required for smaller patients, such as children and infants.

The interior attachment structure 164 may be any suitable structure that can be securely affixed to the body 246. For example, the attachment structure 164 may be formed as a cup-like element having a cylindrical attachment wall 166. However, other structures could also be used. The attachment structure 164 may be secured to the body 246 using any suitable fastening technology, including but not limited to glue, ultrasonic or chemical bonding or welding, structural features such as barbs or hooks, or a tight friction fit.

The leading section 154 of guide element 120 extends outward from the attachment structure 164 through an opening 162 in the body 246. The leading section 154 may be secured to the attachment structure 164 using any suitable fastening technology, including but not limited to glue, ultrasonic or chemical bonding or welding, or interlocking structural features.

Alternatively, the attachment structure 164 may be formed as an integrated part of the leading section 154. As best seen in FIG. 3, the bottom 168 of the attachment structure 164, the attachment wall 166, and the leading section 154 form an evacuated-toroid-shaped space to receive the tip 186 of the insertion section 174 of the inserter element 130. This configuration enables the tip 186 to be held against the attachment structure 164 without piercing the resilient material of the body 246, which would undesirably produce a frictional engagement of these components. A loose engagement between swallowable weight 158 and tip 186 of leading section 154 of inserter element 130 is desirable to allow the swallowable weight 158 to be released from the tip 186 by releasing tension on the guide element 120, causing the swallowable weight 158 to fall away.

Figure 10:
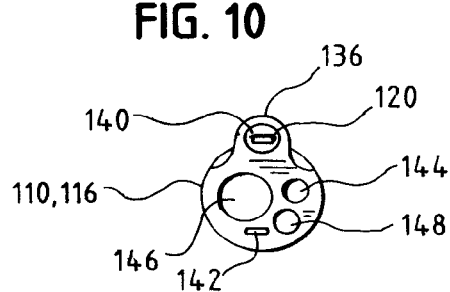
FIG. 10 is a cross-section view of a nasogastric tube 110 of the nasogastric tube insertion system 100 of FIG. 1, taken along section line 10-10 thereof.

As best seen in FIGS. 1 and 8, the nasogastric tube 110 is preferably constructed as an elongate, generally tubular, body structure comprising a main tubular section 112, a proximal end section 114, and a distal end section 116. The distal end section 116 is intended to be inserted into the patient. The proximal end section 114 is intended to remain outside of the patient. The nasogastric tube 110 includes one or more interior bores or lumina extending approximately the length of the tube 110. As best seen in FIG. 10, an exemplary embodiment of nasogastric tube 110 has three interior bores or lumina 144, 146, and 148, but more or fewer lumina could be used depending on the application and the permissible thickness of the nasogastric tube 110. For example, nasogastric tube 110 may have a single lumen for use as a feeding tube to allow the direct introduction of food or nutritional supplements into the patient's stomach. Nasogastric tube 110 may also comprise a radiopaque tracer strip 142 to allow the position of the nasogastric tube 110 to be verified using radiographic or fluoroscopic examination.

The proximal end section 114 may separate into two or more breakout segments, each including one or more of the lumina 144, 146, 148. As best seen in FIG. 1, in an exemplary embodiment, proximal end section 114 separates into a first breakout tube 118, carrying lumen 144, and a second breakout tube 124 carrying lumina 146 and 148. Second breakout tube 124 provides openings 126 and 128 into lumina 146 and 148 to allow connection of the lumina to a source of fluid to be introduced into the stomach, or a vacuum "supply to remove fluid from the stomach, or to allow the lumen to be vented to the atmosphere. First breakout tube 118 has an opening (not shown) into first lumen 144. As best seen in FIG. 1, a one-way valve 122 may be connected to one of the lumina to control ventilation of the stomach.

The distal end section 116 has a leading end 132. Adjacent the leading end 132, there is provided a plurality of openings 134 leading to the interior bores or lumina 144, 146, and 148 and allowing fluid and gas communication between the lumina 144, 146, and 148 and the exterior space surrounding the leading end 132. The opening or openings leading to a particular one of the lumina may be spaced from the openings leading to other lumina as required by the application. For example, if one lumen is assigned to introduce fluids into the stomach, and another lumen is assigned to remove fluids from the stomach, it may be desirable to separate the corresponding openings so that the fluids newly introduced are not immediately removed.

The distal end section 116 of nasogastric tube 110 further comprises a guide element retaining structure 136 adapted to move slidably along guide element 120. As best seen in FIGS. 1 and 10, the guide element retaining structure preferably comprises a generally tubular protrusion or intrusion attached and parallel to proximal end section 114 having a tubular opening 140 to receive the guide element 120. Once the guide element has been inserted, the guide element retaining structure 136 allows the nasogastric tube 110 to move slidably and telescopically along the guide element 120. Thus, the guide element 120 may serve to establish a path for the nasogastric tube 110 to follow as it is inserted through the patient's nasal passages, oropharynx, esophagus, and into the patient's stomach. The leading end 138 and a trailing end 248 of the guide element retaining structure 136 are preferably chamfered to avoid abrading or irritating tissues which are encountered as the nasogastric tube 110 is inserted and removed.

Although the guide element retaining structure 136 is shown in FIGS. 1 and 10, and described herein as a tubular element attached to the distal end section 116, other structures could also be used to form the guide element retaining structure 136 adapted for slidable and/or telescopic movement along the guide element 120. For example, the guide element retaining structure 136 could be formed as one or more loops or retaining tabs attached to the distal end section 116. For another example, the guide element retaining structure 136 could be formed as a tunnel-style bore through an unused portion of the cross section of the nasogastric tube 110. This configuration has the advantage that no enlargement of the cross-sectional size of the nasogastric tube 110 is needed, but it may not be possible to implement if the tube is crowded. As a further alternative to a separate structure 136 dedicated to retaining the guide element 120, features of the distal end 116 of the nasogastric tube 110 may be used to form a guide element retaining structure. For example, guide element 120 could be threaded or telescoped through an aperture placed at or adjacent the tip 132 of the distal end section 116 of the nasogastric tube 110, extend through one of lumina 144, 146, or 148, and could exit through one of the openings or apertures 134 in communication with such lumen and spaced from the tip 132.

The dimensions of the nasogastric tube 110 are non-critical, but must be selected to allow the tube to be inserted through the nasal passages and into the stomach, and to remain there without interfering with the patient's respiration. A smaller diameter, if permitted by the requirements for the lumina inside the tube, is generally preferable in that it minimizes patient discomfort. A nasogastric tube 110 having a diameter of approximately 0.25 inches is believed to be suitable for most adult patients. The length of the nasogastric tube 110 should be long enough to extend into the patient's stomach, with some additional length outside the patient to allow for convenient external connections and to prevent the patient from inadvertently swallowing the proximal end section 114 of the nasogastric tube 110.

The nasogastric tube 110 is preferably constructed of any suitable biocompatible material, having sufficient thickness, flexibility and strength. Because the nasogastric tube 110 will be swallowed and will be subject to digestive acids and enzymes for some period, the material from which the nasogastric tube 110 is constructed is preferably non-porous and highly resistant to attack from such agents. For example, the nasogastric tube 110 may be constructed of a silicone elastomer. Other flexible, biologically inert materials could also be used. The nasogastric tube 110 is preferably transparent or translucent to allow visual inspection of the lumina for proper operation.

FIGS. 14-19 depict several steps in exemplary methods 310, 310a (FIG. 20) according to an aspect of the present invention for use in conjunction with the nasogastric tube insertion system 100 of FIGS. 1-13.

Figure 20:
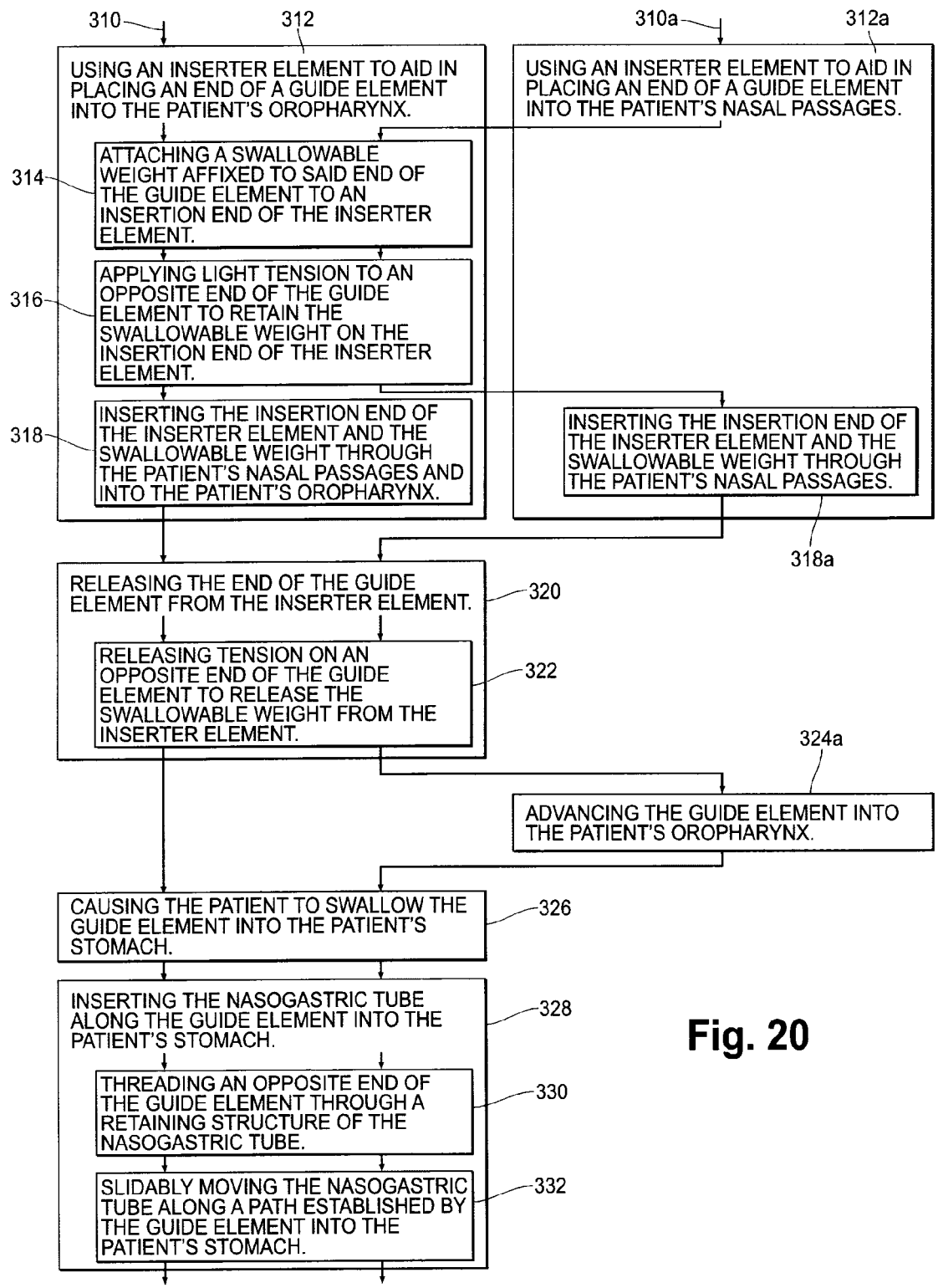
FIG. 20 is a flow diagram depicting steps of exemplary methods 310, 310a of inserting the nasogastric tube insertion system 100 into the patient.

FIG. 20 is a flow diagram depicting steps of exemplary methods 310, 310a. In method 310, the inserter element 130, with the swallowable weight 158 engaged to the insertion end thereof, is used to insert the swallowable weight through the patient's nasal passages and into the oropharynx.

In method 310a, the inserter element 130 is used to insert the swallowable weight through the patient's nasal passages. Then the swallowable weight 158 is released from the end of inserter element 130 and is advanced into the patent's oropharynx, by, for example, gentle longitudinal pressure on the guide element 120 in the direction of the patient's oropharynx.

In other respects, the methods 310 and 310a are similar. The term "step" is used herein to refer to both the general steps associated with one of methods 310, 310a, and to more detailed substeps which may be comprised as part of a more general step. Some steps are optional.

A first group of steps 312, 314, 316 is generally depicted in FIG. 14. The user grasps the handle 176 (FIGS. 1 and 11) of inserter element 130 using a first hand 212. The user places the swallowable weight 158 on the tip 186 of insertion section 174 of inserter element 130 (step 314). The user then uses a second hand 210 to apply light tension on guide element 120, thereby maintaining the swallowable weight 158 in position on the end of inserter element 130 (step 316) A second group of steps is generally depicted in FIG. 15. The user uses the second hand 210 to gently pull the guide element 120 rearward, in order to position the guide element 120 in channel 194 (FIG. 13) on the dorsal surface of inserter element 130. The user must allow controlled slippage of the guide element 120 to allow the second hand to move rearward while maintaining light tension on guide element 120. The user then uses the thumb 214 of the first hand to trap the guide element 120 under light tension against the dorsal surface of the inserter element 130. This prevents the swallowable weight 158 from falling off of the inserter element 130.

In an optional step, the user may transfer the inserter element 130 and guide element 120 from the first hand to the second hand. Subsequent steps assume this has been done.

In another optional step, the user may apply one or more of an anesthetic (such as lidocaine), and a vasoconstrictor (such as epinephrine), to the absorbent material of the swallowable weight 158. The anesthetic numbs the passage to the stomach. The vasoconstrictor causes vasoconstriction of the nasal mucosa allowing for easier passage and decreased bleeding. This step may be performed, for example, by dipping the swallowable weight 158 into a container of these substances. The anesthetic and vasoconstrictor agents may be packaged with the nasogastric tube insertion system 100, to promote their use. Also, the swallowable weight 158 may be pre-moistened with the anesthetic and vasoconstrictor agents by a manufacturer or distributor, to relieve the user of the burden of applying the agents, and to minimize the risk of contamination which might occur in bulk containers of the agents in a clinical environment.

Figure 16:
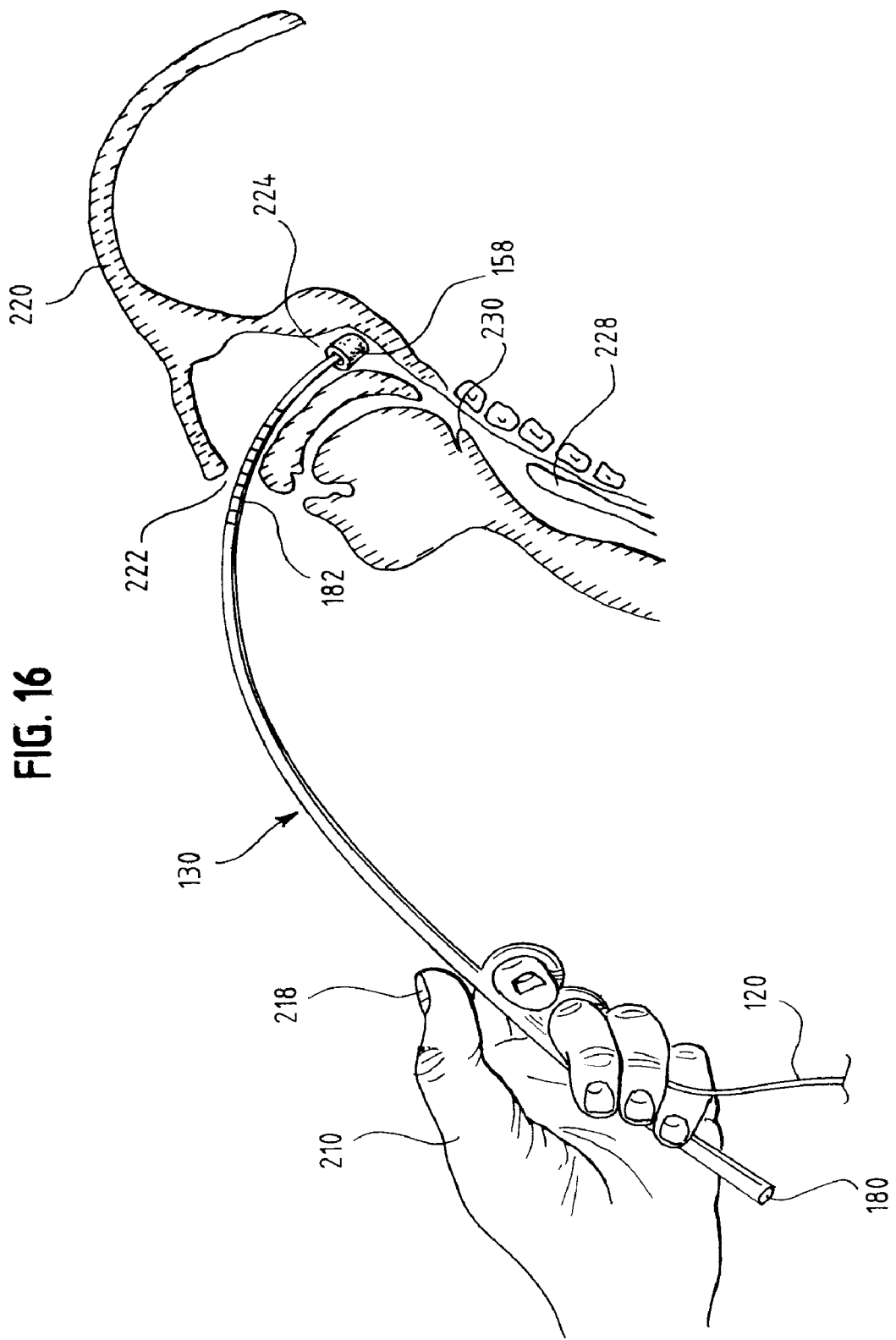
FIG. 16 is a side view and stylized partial cross-section view showing the inserter element 130 and guide element 120, depicting another stage in the method of inserting the nasogastric tube insertion system 100, in which the inserter element 130 and guide element 120 are being inserted through the patient's nasal passages to the nasopharynx or oropharynx.

A third group of steps 318 is generally depicted in FIG. 16. The user inserts the inserter element 130 and guide element 120 through the nostril 222 of patient 220, through the nasal passages, and into the oropharynx 224 (step 318). The user maintains pressure on guide element 120 using the thumb 218 during this process to keep the swallowable weight 158 in position. The user is preferably guided by measurement indicia 182 to insert the inserter element 130 to a predetermined insertion depth measured earlier. For most patients, an optimal predetermined insertion depth may be found by measuring the distance between the patient's earlobe and the tip of the patient's nose.

Figure 17:
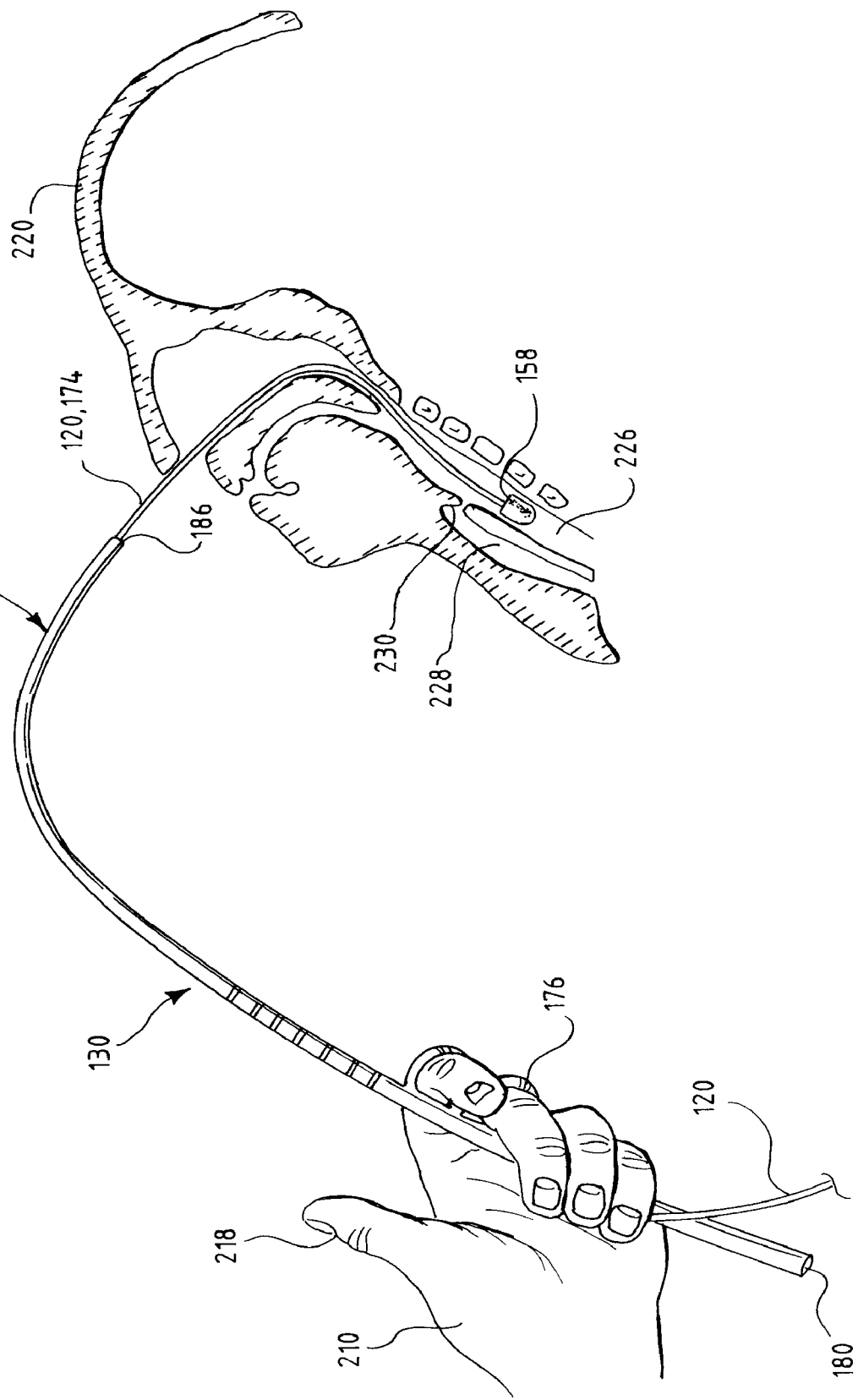
FIG. 17 is a side perspective view and stylized partial cross-section view showing the inserter element 130 and guide element 120, depicting another stage in the method of inserting the nasogastric tube insertion system 100, in which the inserter element 130 is removed and the swallowable weight 158 of the guide element 120 is being swallowed past the epiglottis.

A fourth group of steps 320, 322, 326 is generally depicted in FIG. 17. The user releases thumb 218, thereby relieving pressure on the guide element 120, and freeing the swallowable weight 158, allowing it to fall (steps 320, 322). At approximately the same time, the patient 220 is instructed to swallow the swallowable weight 158 (step 326). The patient may be given some water to sip to assist in swallowing. As a consequence of swallowing, the patient's epiglottis 230 covers the trachea 228, ensuring that the swallowable weight 158 is carried into the esophagus 226, and then into the stomach. The trailing section 152 and proximal end 150 of guide element 120 remains outside the patient. The user then removes the inserter element 130, which is no longer required for this procedure.

Although the steps heretofore described in connection with FIGS. 16-17 contemplate that the inserter 130 be used to place the swallowable weight 158 all the way into the patient's oropharynx 224, it may be preferable in some situations to use the inserter element 130 to place the swallowable weight 158 only part way into the nasal passages—that is, between the nostril 222 and the oropharynx 224. In an alternative submethod 310a according to an aspect of the present invention for use in conjunction with the nasogastric tube insertion system 100 of FIGS. 1-13, the steps of FIGS. 16-17 may be modified as follows: The user inserts the inserter element 130 and guide element 120 through the patient's nostril 222, and into a predetermined location in the nasal passages, but not as far as the oropharynx 224 (step 312a-318a). The user maintains pressure on guide element 120 using the thumb 218 during this process to keep the swallowable weight 158 in position (step 316).

The user is preferably guided by measurement indicia 182 to insert the inserter element 130 to a predetermined insertion depth measured earlier. For most patients, an optimal predetermined insertion depth may be found by measuring the distance between selected benchmarks on the patient's face or body. A shorter inserter element 130 may be used. The user releases thumb 218, thereby relieving pressure on the guide element 120, and freeing the swallowable weight 158 (steps 320, 322). The inserter element 130 may optionally be retracted, or it may be temporarily left in place to support the guide element 120 during advancement of the swallowable weight into the oropharynx.

The user applies gentle longitudinal pressure to guide element 120 to further advance the swallowable weight 158 into the oropharynx 224, noting by feel or by patient reaction when the weight has arrived in the desired position (step 324a). The patient is then instructed to swallow the swallowable weight 158 (step 326). The patient may be given some water to sip to assist in swallowing. As a consequence of swallowing, the patient's epiglottis 230 covers the trachea 228, ensuring that the swallowable weight 158 is carried into the esophagus 226, and then into the stomach. The trailing section 152 and proximal end 150 of guide element 120 remains outside the patient. The user then removes the inserter element 130, if present. The remaining steps of methods 310 and 310a are similar.

Figure 18:
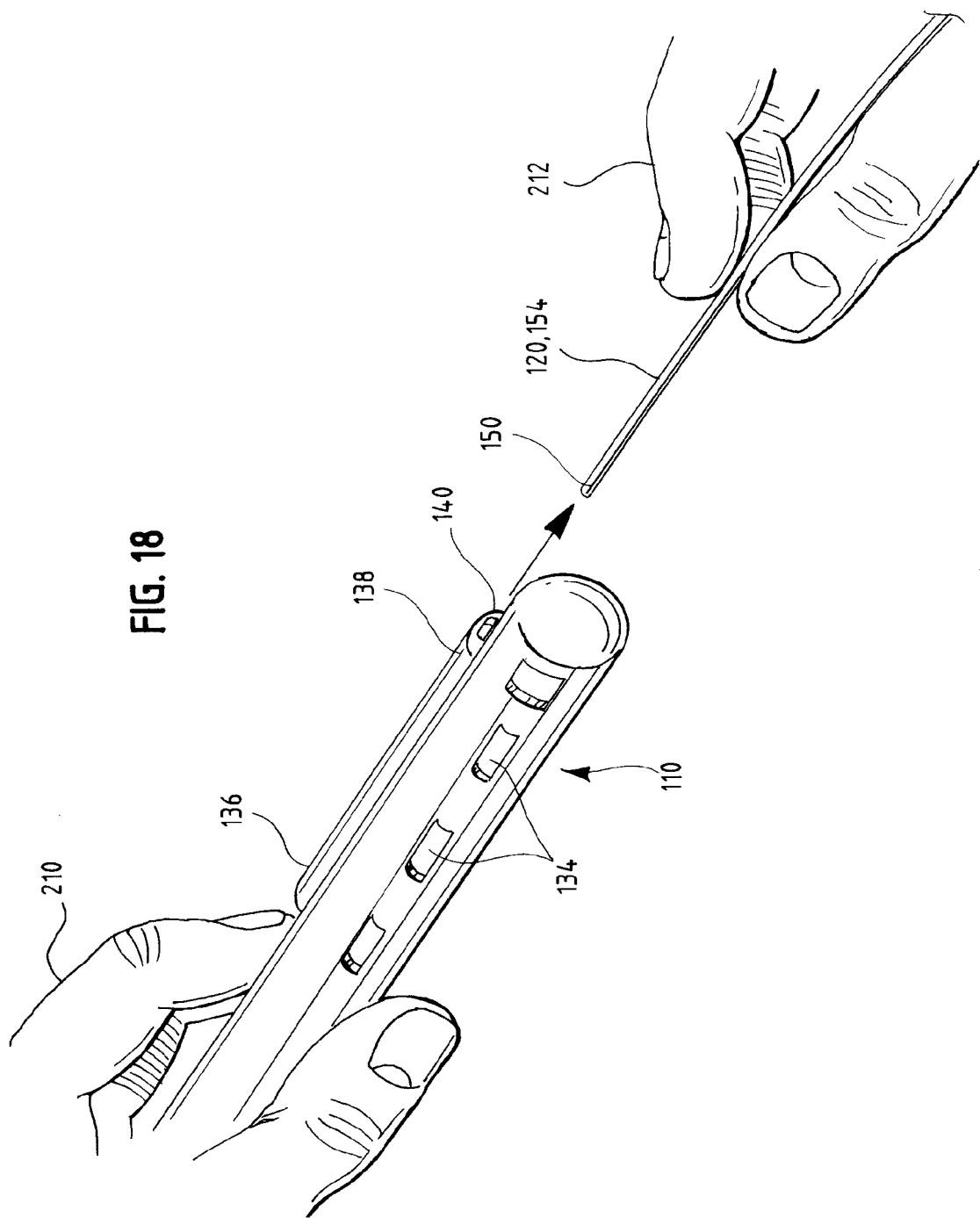
FIG. 18 is a side view showing the nasogastric tube 110 and the guide element 120, depicting another stage in the method of inserting the nasogastric tube insertion system 100, in which the guide element 120 is threaded through an opening of the guide element retaining structure 136 of the nasogastric tube 110.
Figure 19:
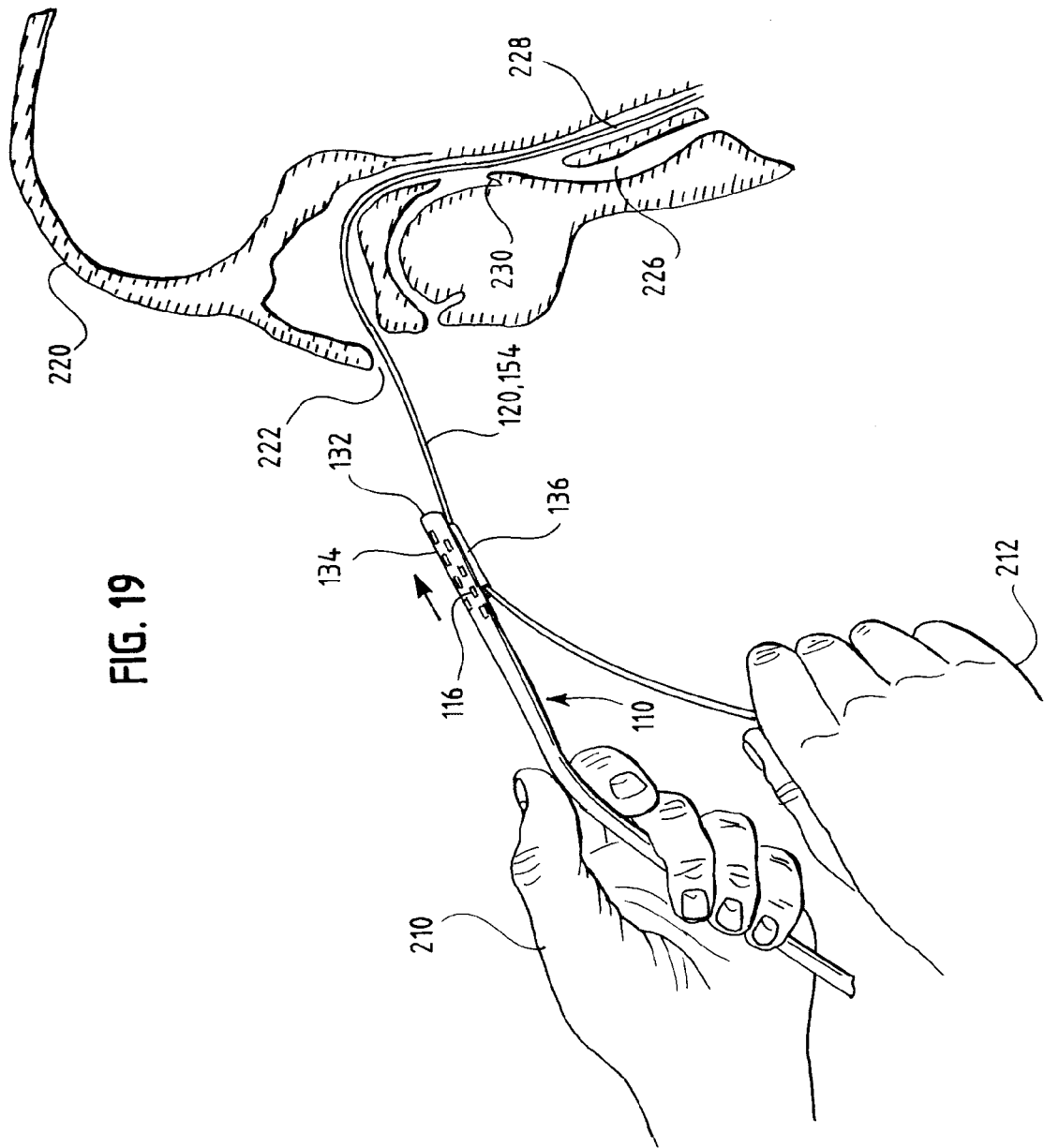
FIG. 19 is a side view and stylized partial cross-section view showing the nasogastric tube 110 and the guide element 120, depicting another stage in the method of inserting the nasogastric tube insertion system 100, in which the nasogastric tube 110 is pushed along the guide element 120 as the tube is inserted into the patient's nasal passage.

A fifth group of steps 328, 330 is generally depicted in FIG. 18. The user threads the proximal end 150 of the guide element 120 through the retaining section opening 140 of the guide element retaining structure 136 of nasogastric tube 110 (step 330). This step is optional; the nasogastric tube 110 may be supplied by the manufacturer, or otherwise distributed to the user, in the condition in which the guide element 120 is already telescoped through the guide element retaining structure 136.

A sixth group of steps 328, 332 is generally depicted in FIG. 20. Holding the guide element 120 firmly in a first hand 212, and the nasogastric tube 110 in a second hand 210, the user pushes the nasogastric tube 110 telescopically along the guide element 120. The user inserts the nasogastric tube 110 through the nostril 222 and the tube safely follows the path established by the guide element 120 into the patient's stomach (step 332). The guide element 120 and nasogastric tube 110 remain together until the nasogastric tube 110 is to be removed. Then, the nasogastric tube 110 and the guide element 120 are removed together. As described further in greater detail, in other embodiments, the guide element 120 may be removed prior to removing the nasogastric tube 110.

Although the shape of the swallowable weight 158 has been shown in FIGS. 1 and as generally cylindrical, there may be situations in which a different shape is advantageous. Especially upon removal of the nasogastric tube 110 and guide element 120, a gentler transition from the thin leading section 154 of the guide element to the full diameter of the swallowable weight 158 may ease passage of the swallowable weight through the patient's esophagus, nasal passages, and the like, and may minimize damage to tissues and deterioration of the weight. FIG. 21 is an enlarged side view of an alternative embodiment 250 of the leading section of guide element 120. FIG. 21 also depicts an alternative embodiment 270 the insertion section of inserter element 130 which may advantageously be used in conjunction with the alternative leading section 250 of guide element 120. FIG. 22 is an enlarged cross-section view of the alternative leading section 250.

FIG. 23 is an enlarged perspective view of the tip 272 of the alternative insertion section 270 of inserter element 130 portion of the alternative leading section 250 of guide element 120. The features of these FIGS. 21-23 will generally be described together. Except for the points of departure mentioned in connection with FIGS. 21-23, guide element 120 and inserter element 130 may be constructed in the same manner, and may have the same properties, as generally described earlier.

As best seen in FIGS. 21-22, alternative leading section 250 preferably has a slender longitudinal portion similar to that of leading section 154 (FIG. 1). Alternative leading section 250 preferably also has a body 252 which may include a first section 254 of generally cylindrical shape adjacent to a second section 258 of generally conical shape at a transition 262. The front or leading edge 256 of body 252 may have a rounded or partially-spherical contour to aid insertion. It is not essential that the shape of the first section 254 be cylindrical, but it is preferable that it have sufficient diameter that the body 252 serve as a weight and be acted upon by the patient's swallowing mechanism, and it may be preferable that the contour be relatively free from large topological features that may interfere with anatomical structures during insertion. It is not essential that the shape of the second section 258 be conical, but is it preferable that its diameter gradually increase from that of the slender longitudinal portion of alternative leading section 250 to the full diameter of the body 252. The transition 262 from the first section 254 to the second section 258 may be so gradual as to be invisible, and these sections may be integrally constructed.

The body 252 is preferably securely attached to the slender longitudinal portion of alternative leading section 250 using an attachment structure 260. For example, the longitudinal portion of the alternative leading section 250 may extend into the body, and an attachment structure 260 may be formed as an anchor or other structure for securely mechanically engaging the body 252. However, the attachment structure 260 may also be formed as any part of leading section 250 in contact with body 252 and fastened thereto using any suitable fastening technology, including but not limited to glue, ultrasonic or chemical bonding or welding, structural features such as barbs or hooks, or a tight friction fit. The body 252 and the alternative leading section 250 may be constructed of materials and attached as described in connection with the swallowable weight 158 of the earlier-described embodiment.

As best seen in FIGS. 21 and 23, alternative insertion section 270 of inserter element 130 may include a relatively slender longitudinal portion 270 and a flared end portion 272 for engaging the body 252 of the swallowable weight of the alternative leading section 250 of guide element 130. The terminal end 276 of the flared end portion 272 may have a conical-concave shape to receive and engage the conical second section 258 of the alternative leading section 250 of the guide element 120. A slot extending along the dorsal surface of the alternative insertion section 270, formed by walls 280, and leading to a central lumen 282 forms a channel for receiving the longitudinal portion of alternative leading section 250, similar in structure and operation to channel 194 of insertion section 174 (FIG. 13).

Although slot 270 and central lumen 282 are shown as separate structures, they could also be formed as an integral U-shaped channel or any other appropriate structure for receiving the longitudinal portion of alternative leading section 270.

It is not essential that the shape of the terminal end 276 exactly mate with the second section 258 of alternative leading section 250, but it is important that the shape be compatible so that when light tension is provided on guide element 120, the body 252 of the alternative leading section 250 is retained on the end of the alternative insertion section 270, and when such tension is released, the body 252 of the alternative leading section falls away. The alternative leading section 250 may be constructed of materials as described in connection with leading section 174 the earlier-described embodiment.

One of skill in the art will appreciate that nasogastric tubes of various designs and functions may be inserted using the inserter element 130, the guide element 120, and the associated methods described earlier. In accord with a further aspect of the present invention, a nasogastric tube adapted for use as a feeding tube may be advantageously used with the aforementioned elements. Feeding tubes are used by medical practitioners in a number of situations, including those where the patient is unable to feed himself or herself, and those where the patient lacks desire to feed.

A nasogastric feeding tube is generally similar to the earlier-described nasogastric tube 110, but has several differences to accommodate its use as a feeding tube. A nasogastric feeding tube generally has a distal end intended for placement into the patient's stomach, a proximal end intended to remain outside the patient, and a main tubular section joining the distal and proximal ends. Because feeding tubes are often left in position in the patient for an extended period, and the tubes are typically used to deliver fluid under slight positive pressure but are not subject to suction, the main tubular section is usually constructed of very flexible material having thin walls to minimize damage and discomfort to the patient. The feeding tube diameter is often smaller than that of other types of nasogastric tube. Typical feeding tubes have a single lumen, but some feeding tubes have more lumina and some feeding tubes are adapted to permit suction to be used to remove material from the stomach.

Figure 24:
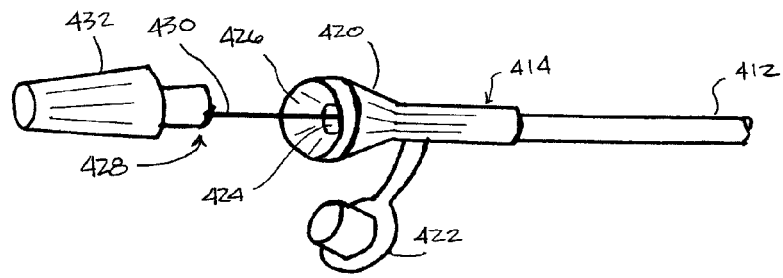
FIG. 24 is a side perspective view of a first embodiment of a proximal end section of an alternate nasogastric tube, in the form of a nasogastric feeding tube, for use in conjunction with the guide element 120 and inserter element 130 of the present invention.
Figure 25:
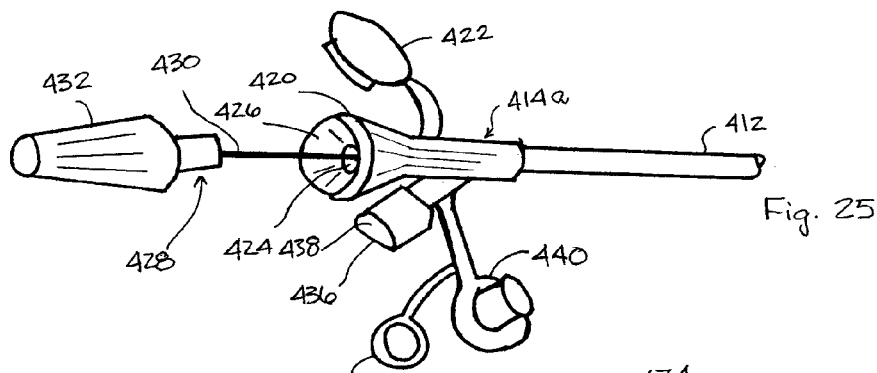
FIG. 25 is a side perspective view of a second embodiment of a proximal end section of an alternate nasogastric tube, in the form of a nasogastric feeding tube, for use in conjunction with the guide element 120 and inserter element 130 of the present invention.
Figure 26:
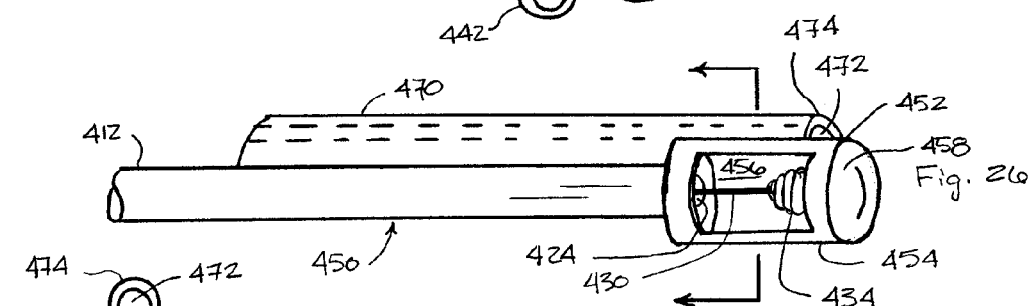
FIG. 26 is a side perspective view of a first embodiment of a distal end section of an alternate nasogastric tube, in the form of a nasogastric feeding tube, for use in conjunction with the guide element 120 and inserter element 130 of the present invention.
Figure 27:
FIG. 27 is a cross section view of the distal end section of FIG. 26, taken along the section lines 27-27 thereof.
Figure 28:
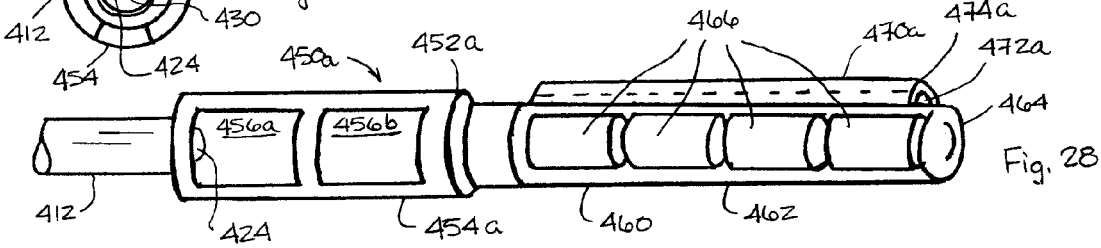
FIG. 28 is a side perspective view of a second embodiment of a distal end section of an alternate nasogastric tube, in the form of a nasogastric feeding tube, for use in conjunction with the guide element 120 and inserter element 130 of the present invention.
Figure 29:
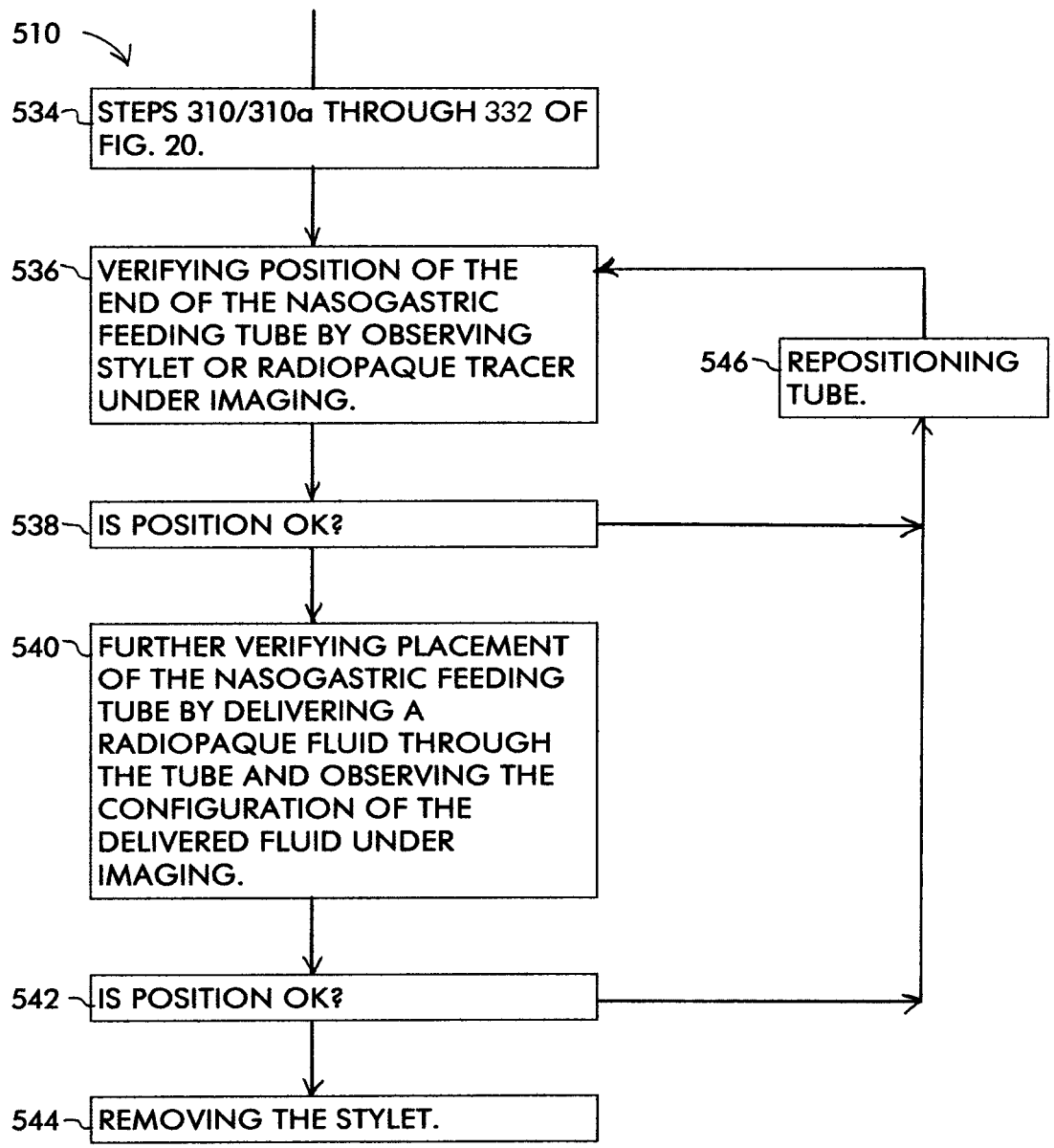
FIG. 29 is a flow diagram depicting steps of exemplary methods 510, 510a of inserting the nasogastric tube insertion system 100 into the patient using a nasogastric feeding tube of the type shown in FIGS. 24-28.

FIGS. 24 and 25 are side perspective views of first and second embodiments 414 and 414*a*, respectively, of proximal end sections of a nasogastric feeding tube which may be used as the nasogastric tube portion of a nasogastric tube insertion system, similar to the nasogastric tube insertion system 100 earlier described. FIGS. 26 and 28 are side perspective views of first and second embodiments 450 and 450*a*, respectively, of distal end sections of a nasogastric feeding tube which may be used as the nasogastric tube portion of a nasogastric tube insertion system. That is, a feeding tube having any of the proximal ends 414 or 414*a*, and any of the distal ends 450 or 450*a*, may be substituted for the feeding tube 110 of nasogastric tube insertion system 100, and used in conjunction with the guide element 120 and inserter element 130 the present invention. FIG. 27 is a cross section view of the distal end section of FIG. 26, viewed toward the proximal end.

Although not shown in the drawings as an integrated unit, the proximal end of the feeding tube is connected to its distal end by the main tubular section 412, and that section is sufficiently long that the distal end may rest in the patient's stomach while the proximal end extends a distance from the patient's nostril to accommodate a connection to a source of nutritional material or other fluid. The main tubular section 412 may be formed as a single integrated component or may be constructed as an assembly of longitudinally mated subsections. Similarly, the main tubular section 412, proximal end 414 or 414*a*, and distal end 450 or 450*a* may be formed as an integrated unit, or may be constructed as separate components and mated together prior to use. The assembly of separate sections may be performed during manufacturing or by the user.

As best seen in FIG. 24, a first embodiment 414 of a feeding tube proximal end includes at least one terminal port housing 420 coupled to the main tubular section 412. The port housing 420 has an opening 426 that forms a port adapted for connection to a source of fluid material (e.g., any appropriate nutritional, hydration, irrigation, or drug product material in fluid form), via appropriate tubing or a connector thereon (not shown). The opening 426 communicates with a lumen 424 of the main tubular section 412, which lumen extends to the distal end of the feeding tube. The opening 426 may have a concave or funnel shape or other appropriate shape for mating with the tubing or connector from the fluid source. A flexible cap 422 is preferably tethered to the housing 420 to allow the opening 424 to be closed to avoid entry of foreign matter.

In feeding tubes which are not designed for use with suction, the walls of the main tubular section 412 may be quite thin and extremely flexible. As a result, it is difficult or impossible to insert the feeding tube though the nasal passages, oropharynx, esophagus, and the like, because any forward pressure on the tube causes it to bend. As best seen in FIG. 24, an optional stylet 428 may be provided to temporarily stiffen the feeding tube to facilitate insertion. The stylet 428 has a handle 432 and a thin wire 430 attached thereto. The stylet wire 430 extends through the lumen 424 of main tubular section 412 to the distal end of the feeding tube. The wire 430 adds stiffness, so that forward pressure may be applied to the tube to advance it into the patient. Where a stylet is used, it may be installed into the feeding tube by a medical professional performing the insertion procedure, or may preferably be installed by the device manufacturer.

If the main tubular structure 412 is constructed of a soft, flexible material, the terminal port housing 420 and related elements are preferably constructed of a suitable stiffer material. Also, if the feeding tube is intended for additional uses, including suction, the walls of the main tubular section 412 may be thicker and constructed of a stiffer, less flexible material. Further, the terminal port housing 420 could be formed integrally with the main tubular section 412 by incorporating one more ports at or near the proximal end thereof.

As best seen in FIG. 25, a second embodiment 414*a* of a proximal end of a feeding tube is generally constructed in a manner similar to that of the first embodiment, and therefore, only the differences between the two will be described.

The second embodiment 414*a* has a second port extension 436 that forms a port adapted for connection to an additional source of fluid material via appropriate tubing or a connector thereon (not shown). The second port extension 436 has an opening 438 in communication with the lumen 424 of main tubular section 412. A cap 440 is preferably tethered to the housing 420 to allow the opening 438 to be closed. An adaptor 442 may also be tethered to the housing 420 or to the cap 440. The adaptor 442 may be optionally inserted into the opening 438 to accommodate a second size or configuration of tubing or connector from the additional fluid source. The second port allows additional fluid to be introduced without disconnecting the first source from the first port. For example, an irrigating fluid may be introduced to clear blockage in the main tubular section.

As best seen in FIGS. 26-27, a first embodiment 450 of a distal end section of a feeding tube has an exit port housing 452 coupled to the main tubular section 412. The housing 452 may have a generally hollow cylindrical shape including a blunt convex tip 458 and cylindrical walls 454 forming a chamber in communication with lumen 424 of the main tubular section 412. Other shapes for housing 452 could also be used. At least one exit "window" or opening 456 is provided in the housing 452 to allow fluid carried by main tubular section 412 to escape the chamber. As best seen in FIG. 27, two opposed window openings may be provided, but any other appropriate configuration could also be used.

Stylet wire 430 extends into the housing and terminates in an end structure 434. The end structure 434 is preferably shaped to removably engage a portion of the housing during feeding tube insertion and to avoid puncturing the feeding tube when the stylet is withdrawn after the feeding tube has been successfully inserted into a desired position. For example, the end structure 434 may be constructed as a tight helical winding of the end of wire 430 into a conical shape. Other shapes and structures could also be used. The stylet may be radiopaque to allow it to be seen using an appropriate imaging procedure.

The distal end section 450 of the feeding further comprises a guide element retaining structure 470 adapted to move slidably along guide element 120, similar to that the guide element retaining structure 136 of FIGS. 1 and 10. The guide element retaining structure 470 preferably comprises a generally tubular protrusion or intrusion attached and parallel to the exit port housing 452 and a portion of the main tubular section 412. The guide element retaining structure 470 has a tubular opening 472 to receive the guide element 120. Once the guide element has been inserted, the guide element retaining structure 470 allows the feeding tube to move slidably and telescopically along the guide element 120. Thus, the guide element 120 may serve to establish a path for the feeding tube to follow as it is inserted through the patient's nasal passages, oropharynx, esophagus, and into the patient's stomach. The leading end 474 and the trailing end of the guide element retaining structure 470 are preferably chamfered to avoid abrading or irritating tissues which are encountered as the feeding tube is inserted and removed.

Although the guide element retaining structure 470 is shown in FIG. 26 and described herein as a tubular element attached to the exit port housing 452 and a portion of the main tubular section 412, the guide element retaining structure could extend only along the exit port housing 452. In addition, structures could also be used to form the guide element retaining structure 470 adapted for slidable and/or telescopic movement along the guide element 120. For example, the guide element retaining structure 470 could be formed as one or more loops or retaining tabs attached to the exit port housing 452. For another example, the guide element retaining structure 470 could be formed as a tunnel-style bore through an unused portion of the cross section of the exit port housing. This configuration has the advantage that no enlargement of the exit port housing 452 is needed, but it may not be possible to implement if the housing is crowded. As a further alternative to a separate structure 470 dedicated to retaining the guide element 120, features of the exit port housing 452 or the main tubular section 412 may be used to form a guide element retaining structure. For example, guide element 120 could be threaded or telescoped through an aperture placed at or adjacent the tip 458 of the exit port housing 452 of the feeding tube, extend through the chamber, and could exit through one of exit "window" openings 456.

If the main tubular section 412 is constructed of a soft, flexible material, the exit port housing 450 and related elements are preferably constructed of a stiffer material.

Also, if the feeding tube is intended for additional uses, including suction, the walls of the main tubular section 412 may be thicker, and a channel or lumen may be formed therein. Further, the exit port housing 452 could be formed integrally with the main tubular section 412 by incorporating one more exit ports at or near the end thereof.

As best seen in FIG. 28, a second embodiment 450a of a distal end of a feeding tube is generally constructed in a manner similar to that of the first embodiment, and therefore, only the differences between the two will be described.

The second embodiment 450a of a distal end section comprises an exit port housing 452a coupled to the main tubular section 412 and a weight section 460 attached to the exit port housing 452a. The housing 452a may have a generally hollow cylindrical shape with cylindrical walls 454a forming a chamber in communication with lumen 424 of the main tubular section 412. Because the weight section 460 is attached to the end of the housing 452a, any suitable end configuration of the housing may be used. A plurality of exit "windows" or openings 456a, 456b, etc., may be provided in the housing 452a to allow fluid carried by main tubular section 412 to escape the chamber. The stylet wire is not shown. The weight section 460 is a generally tubular structure having a cylindrical wall 462 and a blunt tip 464. Other appropriate structural configurations could also be used. One or more weights may be provided interior of walls 462 to facilitate insertion and to maintain the position of the distal end section thereafter. The weights are preferably radiopaque to allow them to be seen under an appropriate imaging procedure. Any other appropriate configuration of exit openings and weights could also be used. For example, a single section could incorporate the weights in the chamber, using a plurality of smaller exit opening to allow escape of fluid while retaining the weights.

A guide element retaining structure 470a is preferably formed on the outside of the weight section 460. The guide element retaining structure 470a preferably comprises a generally tubular protrusion or intrusion attached and parallel to the weight section 460. The guide element retaining structure 470a has a tubular opening 472a to receive the guide element 120. The guide element retaining structure 470a may also be located on the exit port housing 452a, or any of the aforementioned alternatives for the configuration of the guide element retaining structure 470 could also be used.

Although the feeding tube has been described herein as having a single lumen, multiple lumina could be used by providing appropriate terminal and exit ports at proximal and distal ends, respectively. For example, some feeding tubes are used simultaneously to introduce nutritional, hydrating, or irrigational materials, while withdrawing other fluids. If suction is used, it is necessary to select suitable materials and thickness for the walls of the corresponding lumen to avoid collapse. The main tubular section 412 may be provided with a radiopaque tracer strip, wire, or other markings, to allow the position of the feeding tube to be verified even if no stylet or weights are used.

The nasogastric feeding tube may be inserted using a method similar to that described earlier in connection with nasogastric tube 110, but preferably incorporates additional steps of verifying correct positioning of the distal end of the tube. The patient must be cooperative and must be able to swallow. Determining this is a clinical decision that must be made by a medical professional at the time the feeding tube is needed.

According to a further aspect of the invention, FIG. 20 is a flow diagram showing the steps of an example method 510 for inserting a nasogastric feeding tube in conjunction with the a nasogastric tube insertion system described herein. Step 534 encompasses all the steps of either method 310 or 310a of FIG. 20, with corresponding elements of a nasogastric feeding tube substituted for the elements of nasogastric tube 110. At the end of step 534, the feeding tube is believed to have been initially placed into position in the patient's stomach.

In practice, feeding tubes are often incorrectly placed in the patient's duodenum, esophagus, or lungs. Improper placement of a feeding tube in the lungs is extremely dangerous, because the nutritional material can fill the lungs, preventing the patient from breathing, causing permanent lung damage, and in a significant fraction of cases, causing death. Accordingly, it is usually appropriate to verify correct placement using a conventional X-Ray or fluoroscopy. In step 536, a medical professional verifies the position of the distal end section 450 or 450a by observing the position of the stylet end, weights, or the radiopaque tracer using an appropriate imaging modality, such as conventional X-Ray or fluoroscopy. In step 538, the medical professional determines whether the position is acceptable, and if so, the method continues in step 538. If the position is wrong, the method continues in step 546.

Step 540 is a further optional position check. In step 540, a radiopaque substance, such as gastrografin may be delivered through the tube, while the patient is examined under fluoroscopy or another appropriate imaging modality. The pattern of diffusion of the radiopaque substance may be observed to determine whether the distal end section 450 or 450*a* has been properly inserted into the stomach, or improperly, e.g., into the duodenum or the esophagus. In step 542, the medical professional determines whether the position is acceptable, and if so, the method continues in step 544. In step 544, the stylet is removed, and the feeding tube is ready for use. If the position is determined to be wrong, the method continues in step 546.

If, in steps 538 or 542, the position is determined to be wrong, the method continues in step 546. The tube is repositioned, and the method returns to step 536, where the position is again verified.

In some instances, it may be desirable to remove the guide element, while the nasogastric tube remains in position in the patient.

According to a further aspect of the invention, a guide element may be provided having a swallowable weight which may be retracted while the nasogastric tube remains in position. The weight may, for example, be constructed in a way that allows it to change shape or form to enable its retraction through a guide element retaining structure or through the nasogastric tube itself. A nasogastric tube that is adapted to facilitate the withdrawal of the guide element may also be provided.

Figure 30:
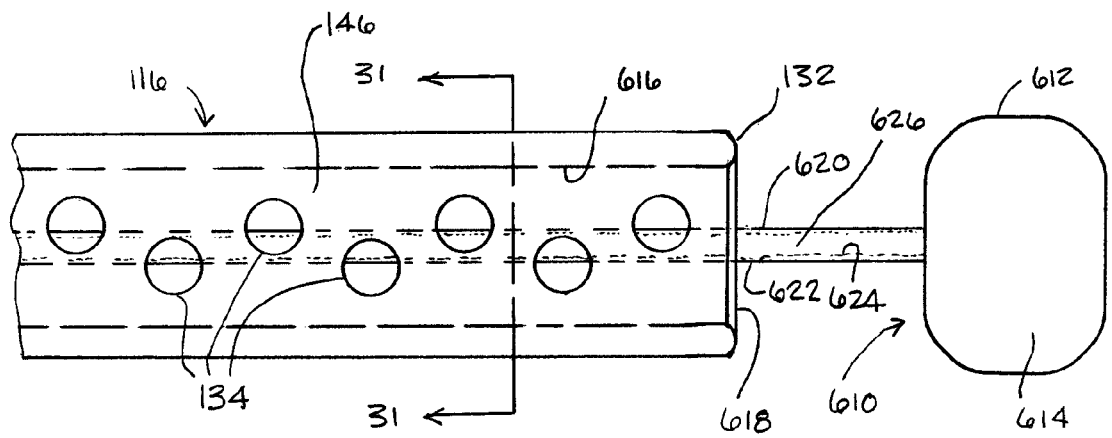
FIG. 30 is a side view showing the leading section of an alternate embodiment of a guide element, and the distal end of an alternate embodiment of a nasogastric tube, constructed according to an aspect of the present invention.
Figure 31:
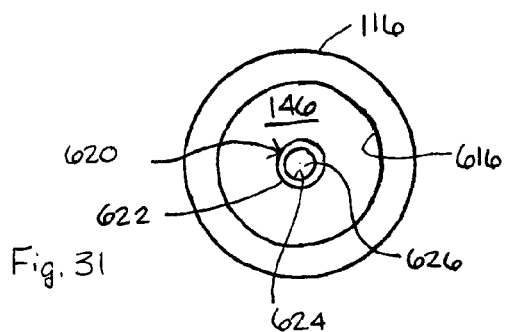
FIG. 31 is a cross section view of the alternate embodiments of the guide element and nasogastric tube of FIG. 30, taken along the section lines 31-31 of FIG. 30.
Figure 32:
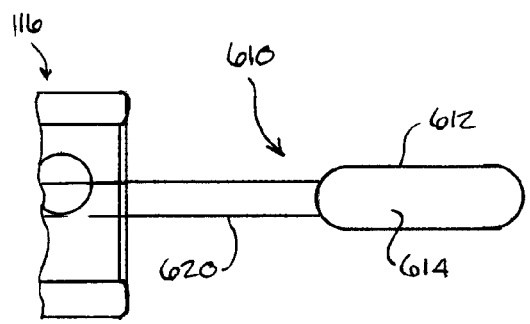
FIG. 32 is a side view showing the alternate embodiments of the guide element and nasogastric tube of FIGS. 30 and 31, showing a weight element thereof in a deflated condition.

According to an aspect of the invention, there is shown in FIG. 30 a side view of the leading section of an alternate embodiment of a guide element, and the distal end of an alternate embodiment of a nasogastric tube, in which the weight is formed as an inflatable sac or balloon, showing the weight in an inflated condition. FIG. 31 is a cross section view of the alternate embodiments of the guide element and nasogastric tube of FIG. 30. taken along the section lines 31-31 of FIG. 30; FIG. 32 is a side view showing the alternate embodiments of the guide element and nasogastric tube of FIGS. 30 and 31, showing the weight a deflated condition.

As best seen in FIGS. 30-32, the distal end section 116 of an alternate embodiment of a nasogastric tube may be formed having at least one lumen 146. The alternate embodiment of the nasogastric tube may generally be constructed as heretofore described in connection with nasogastric tube 110, with modifications as described in this section. Lumen 146 has an inner wall 616, an end opening 618, and a number of side openings or apertures 134. The end and side openings 618 and 134 allow communication of fluids between the lumen and the exterior of the tube. The surfaces of the leading end 132 of the nasogastric tube in the area of the end opening 618 are preferably rounded or smoothed to avoid abrasion or other injury to the patient during insertion of the tube. The particular configuration, including size and arrangement, of the openings shown is an example and may vary in different embodiments. Although only a single lumen is shown, the nasogastric tube could have any appropriate number and size of lumina.

An alternate embodiment 610 of a guide element preferably comprises an inflatable guide element swallowable weight body envelope 612 coupled to a substantially hollow guide element tube 620. The body envelope 612 encloses an interior space 614 for containing fluid, which may be any appropriate gas, such as air, or liquid, such as water. The guide element tube 620 preferably has an exterior wall 622 and inner wall 624 forming a guide element tube lumen 626, which is preferably arranged for fluid communication between the lumen 626 and the interior 614. Swallowable weight body envelope 612 may be inflated by introducing fluid into lumen 626 at the proximal end (not shown) of the guide element 610, as depicted in FIG. 30. The swallowable weight body envelope 612 may be deflated by withdrawing fluid (or allowing the fluid to withdraw) from lumen 626, as depicted in FIG. 32.

The distal end of alternate guide element 610 preferably extends through lumen 146. Lumen 146, or at least one of the lumina if there are several, is preferably large enough to allow passage, for example via slidable movement therethrough, of the alternate embodiment of guide element 610, including the guide element tube 620 and the swallowable weight in its deflated form. Thus, the alternate embodiment of guide element 610 may be withdrawn from the patient while the nasogastric tube remains in a desired position therein.

The body envelope 612 may be constructed of any suitable flexible material which is bio-compatible for insertion in a human patient and compatible with stomach fluids, including but not limited to latex. The body envelope 612 may be formed from an expandable resilient material, similar to that of a conventional balloon, or from a material that does not resiliently expand, such as a bag or pouch. The materials considered appropriate may vary depending on locality-specific practice and regulation. Guide element tube 620 may be constructed from any suitable flexible material which is bio-compatible for insertion in a human patient and compatible with stomach fluids, and which has sufficient strength and rigidity to allow its safe insertion into and withdrawal from the patient. For example, guide element tube 620 may be constructed of a silicone elastomer, but other materials could also be used. The materials considered appropriate may vary depending on locality-specific practice and regulation.

The alternate embodiment of the nasogastric tube system, including the alternate embodiment of the guide element, of FIGS. 30-32 may be inserted in the same manner as earlier-described embodiments. Although the alternate embodiment 610 of the guide element is depicted in FIG. 30-32 as extending through the main lumen of the nasogastric tube, which thus serves as a guide element retaining structure, any lumen, or a guide element retaining structure similar to the retaining structure 136 of FIG. 1, could also be used.

According to a further aspect of the invention, the swallowable weight of the guide element may be constructed from a material which ablates, e.g., via dissolution, disintegration, melting, etc., in the presence fluids present in the patient's stomach to allow the remainder of the guide element to be withdrawn without disturbing the position of the nasogastric tube.

According to an aspect of the invention, there is shown in FIG. 33 the leading section of an alternate embodiment 630 of a guide element with a swallowable weight thereof having a first example configuration. The alternate embodiment 630 of the guide element of FIG. 33 may generally be constructed as heretofore described in connection with guide element 120, with modifications as described in this section. The guide element 630 preferably comprises a guide element leading section 154 generally constructed as earlier described. A swallowable weight in a first example configuration 640 is attached to the guide element leading section 154 near the end 648 thereof. In the first example configuration, swallowable weight 640 preferably has a generally cylindrical body section 642, an end section 644 having rounded or smoothed corners, and a conical tail section 646. However, other configurations could also be used. The rounded or smoothed corners help avoid abrasion or other injury to the patient during insertion, removal, or swallowing of the guide element 630. The conical tail section 646 may mate or engage a corresponding structure on the insertion section 174 of inserter element 130. This prevents the swallowable weight 640 from falling off the end of inserter element 130 if some slack occurs in the guide element 120.

Swallowable weight 640 is preferably constructed from a material that ablates in the presence of stomach fluids or the temperature present in the body. The term "ablate" and terms derived therefrom are used herein to refer to any process where the material of the swallowable weight 640, initially in a solid or cohesive form, dissolves, disintegrates, melts, sublimates, decomposes, falls away, erodes, softens to allow reshaping with minimal force, or the like, when exposed to stomach fluids or to the temperature present in the body, such that thereafter, the weight either no longer exists as a relatively solid mass attached to the guide element 120 or no longer provides a barrier or resistance to withdrawal of the guide element without disturbing the nasogastric tube. The ablation preferably occurs within a short time after arrival of the swallowable weight 640 in the stomach, and does not require digestion of the weight. The time acceptable for the ablation to occur may depend on the application but may, for example, be less than about five minutes. The material is preferably bio-compatible for insertion in the patient. Prior to exposure to stomach fluids, the material is preferably substantially solid; however, the material may exhibit a rigidity within a range extending from completely rigid to a rubbery or gelatinous flexibility. The swallowable weight 640 may be formed using any appropriate method and technology, including but not limited to molding, casting, depositing, precipitating, compressing, or sintering the material about the end 648 of guide element leading section 154. The swallowable weight 640 may be formed, for example, from a liquid or fluid material which sets due to chemical action or temperature, including a gelatin. An example of such a material which is known for use for pharmaceutical formulations and approved in the U.S. is a gelatin compound, which may include glycerin. The swallowable weight 640 may also be formed from a powder which is compressed or sintered to form a generally solid mass. An example of such a material which is known for use for pharmaceutical formulations and approved in the U.S. is compressed glucose. Other materials could also be used, and any appropriate manner of coupling or attaching the swallowable weight 640 to the guide element leading section 154 could be used. The leading section 154 could also be constructed of a material that is soluble in stomach fluids, or disintegrates or becomes extremely soft when exposed to stomach fluids, or changes from a solid to liquid state when exposed to stomach fluids.

According to an aspect of the invention, there is shown in FIG. 34 the leading section of an alternate embodiment 632 of a guide element with a swallowable weight thereof having a second example configuration. The guide element 632 of FIG. 34 may generally be constructed as heretofore described in connection with guide element 630, with modifications as described in this section. The guide element 632 preferably comprises a guide element leading section 154 generally constructed as earlier described. A swallowable weight in the second example configuration 650 is attached to the guide element leading section 154 near the end 648 thereof. In the second example configuration, swallowable weight 650 preferably has a generally cylindrical body section 652, an end section 644 having rounded corners, and a tail section 654 also having rounded corners. However, other configurations could also be used. Swallowable weight 650 may be constructed and may use materials as earlier described for swallowable weight 640.

According to an aspect of the invention, there is shown in FIG. 35 the leading section of an alternate embodiment 634 of a guide element with a swallowable weight thereof having a third example configuration. The guide element 634 of FIG. 35 may generally be constructed as heretofore described in connection with guide element 630, with modifications as described in this section. The guide element 634 preferably comprises a guide element leading section 154 generally constructed as earlier described. A swallowable weight in the third example configuration 656 is attached to the guide element leading section 154 near the end 648 thereof. In the third example configuration, swallowable weight 656 preferably has a generally cylindrical body section 658, an end section 644 having rounded corners, and a tail section having a concave conical wall 660 forming a generally conical opening 662. The opening 662 facilitates a loose engagement of the swallowable weight 656 with the insertion section 174 of inserter element 130 in a manner similar to that shown in FIG. 12 and described in connection therewith. This prevents the swallowable weight 656 from falling off the end of the inserter element 130 if some slack occurs in the guide element 120. Other configurations of swallowable weight 656 could also be used. Swallowable weight 656 may be constructed and may use materials as earlier described for swallowable weight 640.

According to an aspect of the invention, there is shown in FIG. 36 the leading section of an alternate embodiment 636 of a guide element with a swallowable weight thereof having a second example configuration. The guide element 636 of FIG. 34 may generally be constructed as heretofore described in connection with guide element 630, with modifications as described in this section. The guide element 636 preferably comprises a guide element leading section 154 generally constructed as earlier described. A swallowable weight in the fourth example configuration 664 is attached to the guide element leading section 154 near the end 648 thereof. In the fourth example configuration, swallowable weight 664 preferably has a generally cylindrical body section 666, an end section 644 having rounded corners, and a tail section having an end wall 668, a cylindrical inner wall 670, and a base wall 672, forming a generally cylindrical depressed opening 674. The opening 674 facilitates a loose engagement of the swallowable weight 664 with the insertion section 174 of inserter element 130 in a manner similar to that shown in FIG. 12 and described in connection therewith. This prevents the swallowable weight 664 from falling off the inserter element 130 if some slack occurs in the guide element 120. The corner between body section 666 and tail section end wall 668 is preferably rounded or smoothed to avoid abrasion or other injury to the patient during insertion, removal, or swallowing of the guide element 636. However, other configurations of swallowable weight 664 could also be used. Swallowable weight 650 may be constructed and may use materials as earlier described for swallowable weight 640.

According to a further aspect of the invention, retaining structures may be provided on the guide element leading section 154 near the end 648 thereof to improve engagement between the leading section 154 and the swallowable weight, e.g., 640, 650, 656, 654. The retaining structures may be needed or helpful if the material from which the swallowable weight is constructed is not completely rigid, or if the material does not adhesively attach to the surface of guide element leading section 154.

According to an aspect of the invention, there is shown in FIG. 37 a side view of an example embodiment 676 of the leading section 154 of the guide element 120 having retaining structures 678 constructed thereon. In this example embodiment 676, the retaining structures 678 are formed as disk-shaped elements extending transversely from the leading section 154 near the end 648 thereof. Any appropriate swallowable weight (not shown) may be used with the retaining structures 678, and the weight preferably surrounds the retaining structures, at least until the weight arrives in the patient's stomach.

According to an aspect of the invention, there is shown in FIG. 38 a side view of an example embodiment 680 of the leading section 154 of the guide element 120 having retaining structures 682 constructed thereon. In this example embodiment 680, the retaining structures 682 are formed as generally conical cup-shaped elements extending from the leading section 154 near the end 648 thereof. Any appropriate swallowable weight (not shown) may be used with the retaining structures 682, and the weight preferably surrounds the retaining structures, at least until the weight arrives in the patient's stomach.

Figure 39:
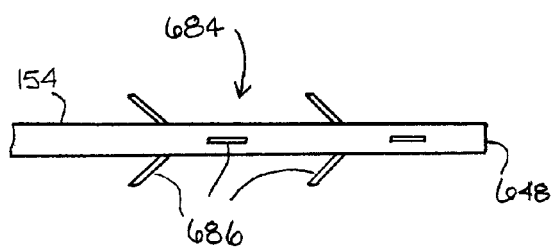
FIG. 39 is a side view showing the leading section of an alternate embodiment of a guide element before the weight element thereof is installed, depicting a third example configuration of members for retaining the weight element.

According to an aspect of the invention, there is shown in FIG. 39 a side view of an example embodiment 684 of the leading section 154 of the guide element 120 having retaining structures 686 constructed thereon. In this example embodiment 684, the retaining structures 686 are formed as spike-shaped elements extending from alternate radial positions of the leading section 154 near the end 648 thereof. Any appropriate swallowable weight (not shown) may be used with the retaining structures 686, and the weight preferably surrounds the retaining structures, at least until the weight arrives in the patient's stomach.

Figure 40:
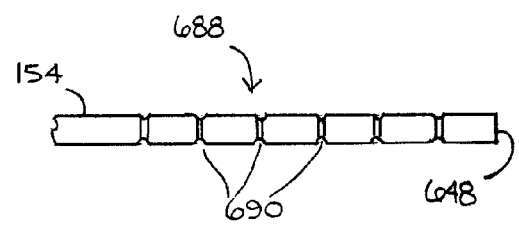
FIG. 40 is a side view showing the leading section of an alternate embodiment of a guide element before the weight element thereof is installed, depicting a fourth example configuration of members for retaining the weight element.

According to an aspect of the invention, there is shown in FIG. 40 a side view of an example embodiment 688 of the leading section 154 of the guide element 120 having retaining structures 690 constructed thereon. In this example embodiment 688, the retaining structures 690 are formed as a plurality of small spaced indentations in the leading section 154 near the end 648 thereof. The retaining structures 690 may be ring-like indentations extending around the entire circumference of the leading section 154, but could also extend less than the entire circumference or could take the form of dimples. The retaining structures 690 may be regularly or irregularly spaced. Any appropriate swallowable weight (not shown) may be used with the retaining structures 690, and the weight preferably surrounds the retaining structures, at least until the weight arrives in the patient's stomach The retaining structures 678, 682, 686, 690 may also be formed in other appropriate shapes. The retaining structures 678, 682, 686, 690 may be formed integrally with the guide element leading section 154, for example by molding, or may be applied to leading section 154 after its formation. The retaining structures 678, 682, 686, 690 may be constructed of any appropriate material, and are preferably flexible and adapted to minimize any abrasion or injury to the patient during insertion, removal, or swallowing of the guide element. The retaining structures are preferably sized to permit removal of the guide element through either the nasogastric tube (if the guide element is threaded through a lumen thereof as depicted in FIGS. 30-32), or the guide element retaining structure 136 (if the guide element is threaded through such a structure as depicted in FIG. 1).

Figure 41:
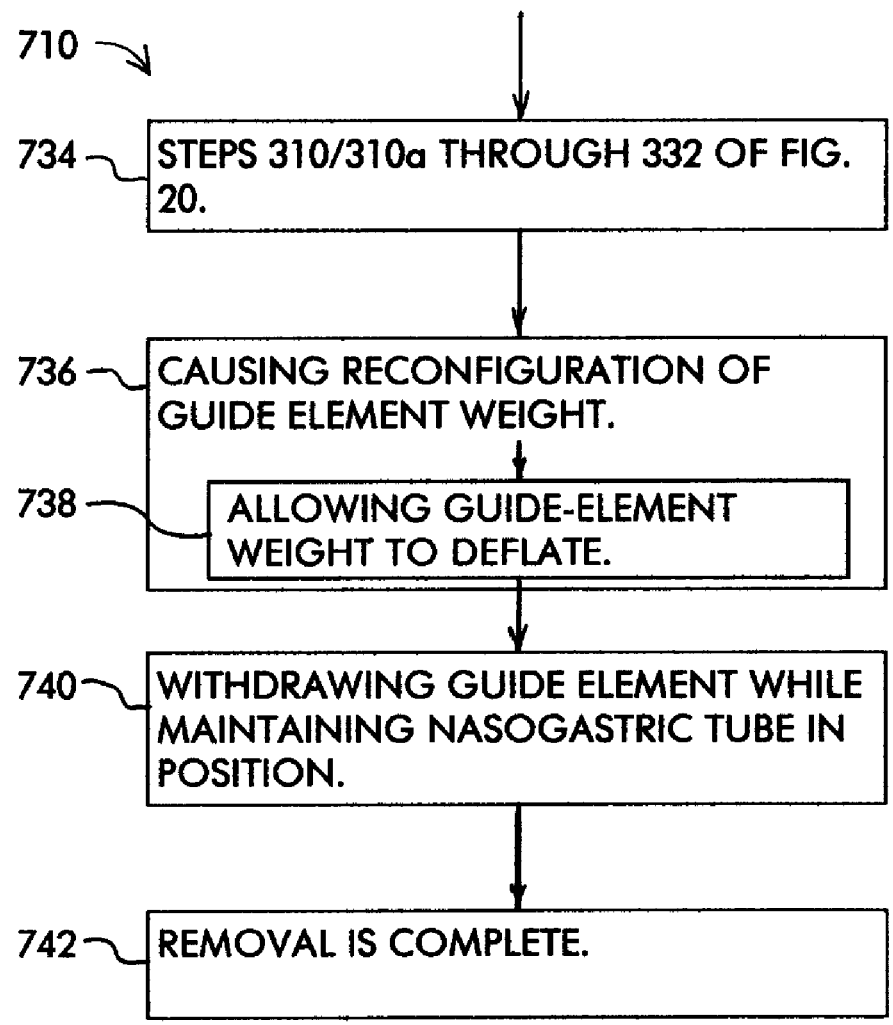
FIG. 41 is a flow diagram showing an example method according to an aspect of the invention for reconfiguring the shape of a guide element, such as that shown in FIGS. 30-32, and removing the guide element while the nasogastric tube remains in place.

According to a further aspect of the invention, there is shown in FIG. 41 a flow diagram of a method 710 for use in removing a guide element of the type shown in FIGS. 30-32 when used in conjunction with a nasogastric tube of the type shown in FIGS. 30-32. Step 734 incorporates steps 310 or 310*a* through step 332 of FIG. 20, at the end of which, the guide element, including the swallowable weight thereof, in its inflated condition, has been positioned in the patient's stomach, and the nasogastric tube has been inserted into the patient's stomach using the guide element. The swallowable weight may be inflated as part of the manufacturing process or may be inflated by the user in preparation for its introduction into the patient.

In step 736, the user causes reconfiguration of the swallowable weight to enable its withdrawal from the patient while the nasogastric tube remains in position. The implementation of step 736 may be further defined by optional substep 738, in which the user allows the guide element to deflate. The user may accomplish this by allowing fluid to exit the lumen 626 of the guide element, or by actively withdrawing fluid through the lumen.

Figure 42:
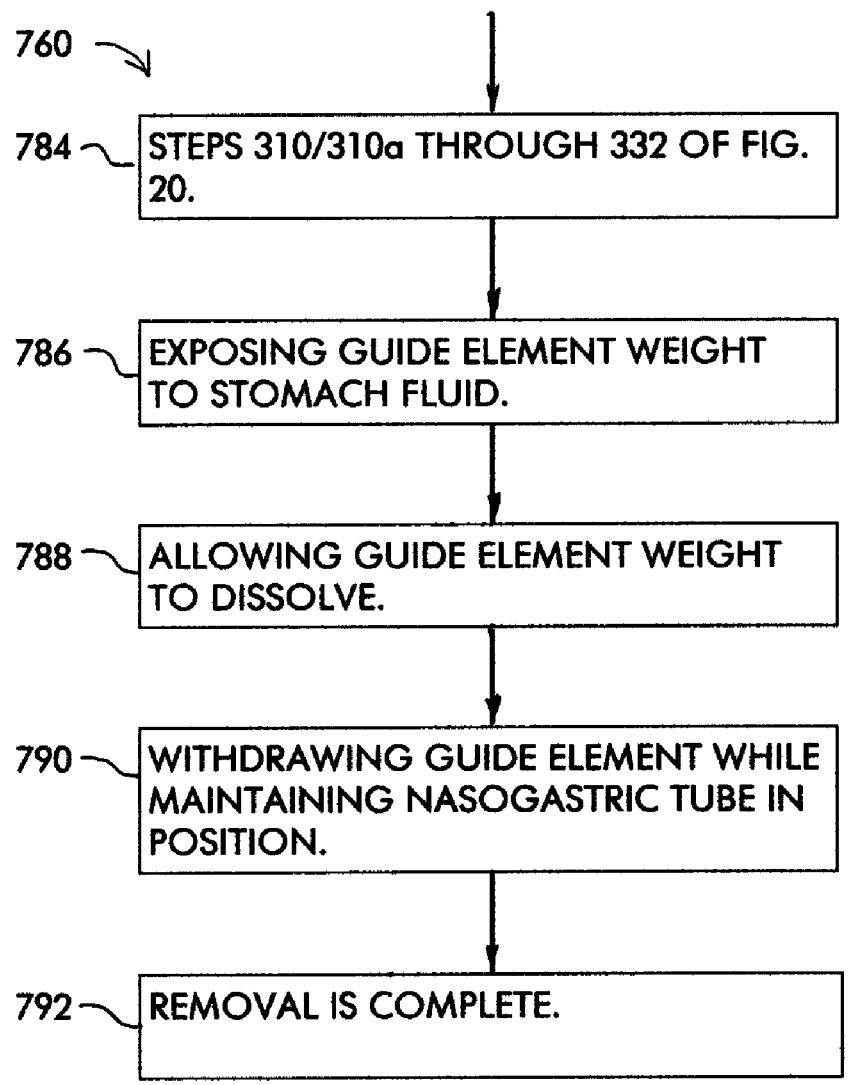
FIG. 42 is a flow diagram showing an example method according to an aspect of the invention for reconfiguring the shape of a guide element, such as that shown in FIGS. 33-40, and removing the guide element while the nasogastric tube remains in place.

In step 740, the user withdraws the guide element from the patient while maintaining the nasogastric tube in position. In step 742, removal of the guide element is complete. According to a further aspect of the invention, there is shown in FIG. 42 a flow diagram of a method 760 for use in removing a guide element of the type shown in FIGS. 33-36, when used in conjunction with a nasogastric tube of the type shown in FIG. 1 or FIGS. 30-32. Step 784 incorporates steps 310 or 310*a* through step 332 of FIG. 20, at the end of which, the guide element, including the swallowable weight thereof, has been positioned in the patient's stomach, and the nasogastric tube has been inserted into the patient's stomach using the guide element.

In step 786, the guide element weight is exposed to stomach fluid. In step 788, the guide element weight is allowed to dissolve, disintegrate, soften, melt, or the like, enabling the guide element leading section 154 to be withdrawn without disturbing the position of the nasogastric tube. In step 790, the user withdraws guide element from the patient while the nasogastric tube is retained in position. In step 792, removal of the guide element is complete.

According to a further aspect of the invention, the nasogastric tube or the guide element may incorporate a chemical-property indicating medium to facilitate verification that the nasogastric tube has been inserted properly into the patient's stomach, and has not been inserted into the lung or other undesirable location. The fluids present in a patient's stomach have an acidic pH below 5.0, while fluids present in locations into which it is possible to erroneously insert the nasogastric tube generally have pH above 5.0. By exposing the indicating medium to the fluids surrounding the distal end of the nasogastric tube, the indicating medium enables the user to verify that the pH of those fluids is below 5.0, thus confirming correct insertion of the nasogastric tube. If the indicating medium is incorporated in the nasogastric tube, the fluids surrounding the distal end of the tube may be aspirated through the tube and into contact with the medium, the condition of which may then be observed by the user. If the indicating medium is incorporated in the guide element, the fluids surrounding the distal end of the tube will come in contact with the medium without additional overt action by the user, although the guide element must subsequently be withdrawn from the patient so that the condition of the medium may be observed. The indicator may generally be used to obtain a measurement of the gastric pH. This measurement may be employed for purposes in addition to establishing correct insertion of the nasogastric tube, including determination that the stomach is prepared to receive a therapeutic agent, or that an appropriate quantity of a therapeutic agent affecting pH, has been introduced. As an alternative to a pH-sensitive medium, media indicating chemical properties other than pH, which may verify correct insertion of the nasogastric tube, signal incorrect insertion of the nasogastric tube, or verify correct or sufficient introduction of a therapeutic, buffering, or irrigation agent, could also be used.

According to an aspect of the invention, there is shown in FIG. 43 a side view of an example embodiment 810 of a nasogastric tube in which a chemical-property indicating medium is incorporated near the proximal end section 114 thereof. FIG. 44 is a cross section view of the example embodiment 810 taken along section lines 44-44 of FIG. 43. The example embodiment 810 may be generally constructed in a manner similar to the nasogastric tube 110 of FIG. 1, with modifications described in this section.

As best seen in FIGS. 43-44, nasogastric tube 810 preferably comprises a generally tubular proximal end section 114 having an interior wall 814 forming at least one lumen 146. If plural lumina are provided in tube 810, the lumen 146 is preferably the one adapted for use in aspirating fluid near the distal end of the tube. The nasogastric tube 810 preferably includes a section 812 for housing a chemical property indicating medium 820. Section 812 may be enlarged, compared to the diameter of other sections of the nasogastric tube. A channel 822 is preferably provided in which the chemical property indicating medium 820 is captured. Several openings 816 are preferably provided between the main bore of lumen 146 and the channel 822 to allow communication of fluid between the lumen 146 and the channel 822. The openings 816, channel 822, and medium 820 are preferably adapted such that when fluid is present in lumen 146, it inundates channel 822 and exposes medium 820.

Medium 820 preferably furnishes a visual indication of a chemical property, such as pH, which may, for example, be manifested as a change in color, reflectivity, or the like. Section 812 is preferably clear or translucent to allow the medium 820 to be viewed externally. The shape of section 812 may act as a magnifying lens to allow a small medium to be easily viewed. Any appropriate chemical-property indicating medium, including but not limited to litmus, pH indicating strips, paper, cloth, or any other substrate impregnated with or bearing a pH indicator, or the like, may be used to implement medium 820. The position and size of section 812 is preferably selected such that the condition of the indicator strip is visually apparent when fluids are initially aspirated through lumen 146 so that the user need not take any additional steps in order to confirm correct insertion of the nasogastric tube in the patient's stomach.

According to a further aspect of the invention, there is shown in FIG. 45 a side view of an additional example embodiment 830 of a nasogastric tube in which a chemical-property indicating medium is incorporated near the proximal end section 114 thereof. There is shown in FIG. 46 a side view of an additional example embodiment 840 of a nasogastric tube in which a chemical-property indicating medium is incorporated near the proximal end section 114 thereof. FIG. 47 is a cross section view of the embodiment 830 taken along the section lines 47-47 thereof. FIG. 48 is a cross section view of the embodiment 840 taken along the section lines 48-48 thereof. The example embodiments 830 and 840 may be generally constructed in a manner similar to the nasogastric tube 110 of FIG. 1, with modifications described in this section.

As best seen in FIGS. 45-48, each of nasogastric tubes 830 and 840 preferably comprises a generally tubular proximal end section 114 having an interior wall 814 forming at least one lumen 146. If plural lumina are provided in tube 830 or 840, the lumen 146 is preferably the one adapted for use in aspirating fluid near the distal end of the tube. Nasogastric tube 830 comprises a chemical-property indicating medium applied to the interior wall 814 in the form of a plurality of indicating elements 832 spaced circumferentially along the interior wall 814. Nasogastric tube 840 comprises a chemical-property indicating medium applied to the interior wall 814 in the form of an indicating element 842 that covers the circumference of the interior wall 814. These particular configurations of the indicating elements 832 and 842 are examples. Other configurations could also be used.

The indicating elements 832 and 842 may be formed using any suitable chemical-property indicating medium or substance, including but not limited to a coating, litmus, pH-indicating strips, paper, cloth, or the like. For example, the medium may be formed as a coating or gelatin bearing phenolphthalein. The term medium is also intended to refer to any indicating substance, regardless of whether or not the indicating chemical or component is carried in or on a substrate, matrix, or similar carrier. Other indicating media could also be used. If the medium is integrated with a substrate such as a paper strip, such substrate is preferably applied to the interior wall 814 using an appropriate adhesive or fastening technology, which may include infrared or ultrasonic bonding. The positions and sizes of the indicating elements 832 and 842 are preferably selected such that the condition of the indicating elements is visually apparent when fluids are initially aspirated through lumen 146, so that the user need not take any additional steps in order to confirm correct insertion of the nasogastric tube in the patient's stomach. In some applications, aspirated fluid that contacts the indicating medium may be reintroduced into the patient or may otherwise come in contact with the patient.

Also, the indicating medium must be firmly attached or adherent to the interior wall 814, or particles or fragments of the indicating medium itself may be inadvertently introduced into the patient through the nasogastric tube or may otherwise contact the patient. In such applications, an indicating medium is preferably selected for bio-compatibility to avoid any potentially toxic effects.

Figure 49:
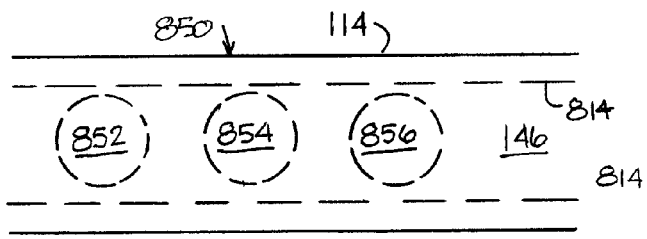
FIG. 49 is a side view of the further alternate embodiment of a nasogastric tube, showing a chemical-property indicating medium thereof in a third example configuration.

According to a further aspect of the invention, there is shown in FIG. 49 a side view of an additional example embodiment 850 of a nasogastric tube in which a chemical-property indicating medium is incorporated near the proximal end section 114 thereof.

As best seen in FIG. 49, a plurality of distinct indicating elements, such as 852, 854, and 856 are provided, each having a medium for visually and distinctly indicating a different chemical property or a different value of a chemical property. The indicating elements 852, 854, and 856 may, for example, change appearance to indicate different pH thresholds have been sensed, or may change appearance to indicate the presence or absence of specific chemicals, proteins, or other detectable components in the fluid aspirated from the vicinity of the distal end of the nasogastric tube. This would give a measurement of gastric pH, as well as verify proper placement of the nasogastric tube. The activated appearance of each of the indicating elements 852, 854, 856 may be visually distinctive. For example, they may appear as distinguishably different colors, thereby minimizing ambiguity as to which indicators are activated. Although the indicating elements are shown in the shape of dots, any suitable shape could also be used, and the elements may be provided in any practical size and number. Any suitable indicating media could be used to implement the indicating elements 852, 854, and 856, such as those described in connection with the embodiments 830 and 840 of FIGS. 45-46.

Figure 50:
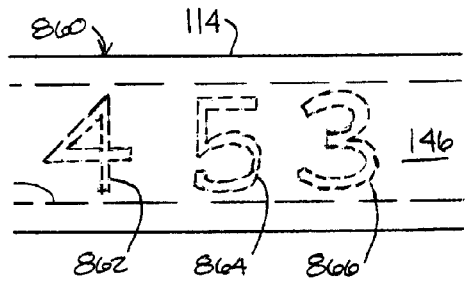
FIG. 50 is a side view of the further alternate embodiment of a nasogastric tube, showing a chemical-property indicating medium thereof in a fourth example configuration.

According to a further aspect of the invention, there is shown in FIG. 50 a side view of an additional example embodiment 860 of a nasogastric tube in which a chemical-property indicating medium is incorporated near the proximal end section 114 thereof. As best seen in FIG. 50, a plurality of distinct indicating elements, such as 862, 864, and 866 are provided, each having a medium for visually and distinctly indicating a different chemical property or a different value of a chemical property, and each having a different shape, size, or other characteristic so that there is no ambiguity as to which indicators are activated. The indicating elements 862, 864, and 866 may, for example, change appearance to indicate different pH thresholds have been sensed, or may change appearance to indicate the presence or absence of specific chemicals, proteins, or other detectable components in the fluid aspirated from the vicinity of the distal end of the nasogastric tube. The shape, size, or other characteristics of the indicating elements may be selected to correspond to the property indicated. By way of example but not limitation, the indicating elements 862, 864, and 866 may be designed to change appearance when fluid pH crosses specific pH thresholds of 4.0, 5.0, and 3.0, respectively, and the indicating elements may be formed as recognizable characters, symbols, or glyphs corresponding to these thresholds. Other distinctive shapes and forms and other schemes defining correspondence between the visual distinctiveness of the indicating element and the property being sensed could also be used. The activated appearance of each of the indicating elements 862, 864, 866 may be visually distinctive in ways in addition to their shape, for example, they may appear as distinguishably different colors, to further minimize ambiguity as to which indicators are activated. Any suitable indicating media could be used to implement the indicating elements 862, 864, and 866, such as those described in connection with the embodiments 830 and 840 of FIGS. 45-46.

Figure 51:
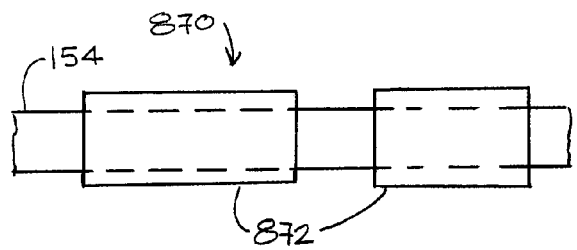
FIG. 51 is a side view of the leading section of a further alternate embodiment of a guide element, showing a chemical-property indicating medium thereof in a first example configuration.

According to a further aspect of the invention, there is shown in FIG. 51 a side view of an additional example embodiment 870 of a guide element with which a chemical-property indicating medium is incorporated on or near the leading section 154 thereof. Guide element 870 may generally be constructed as heretofore shown and described in connection with guide element 120 (FIG. 1), 610 (FIG. 30) or 630 (FIG. 33), with modifications as described in this section. As best seen in FIG. 51, one or more indicating elements 872 are provided on the outer surface of the leading section 154 of the guide element, each having a medium for visually indicating a chemical property. The indicating elements 872 are exposed to fluids in the vicinity of the end of the leading section 154. When the guide element is withdrawn from the patient, the indicating elements are visually apparent and can be used to confirm that the guide element and nasogastric tube were properly inserted in the patient's stomach. Different, visually distinctive indicating elements may be used to indicate different chemical properties or values thereof, as described more fully in connection with embodiment 850 of FIG. 49. Any suitable indicating media could be used to implement the indicating elements 872, such as those described in connection with the embodiments 830 and 840 of FIGS. 45-46.

Figure 52:
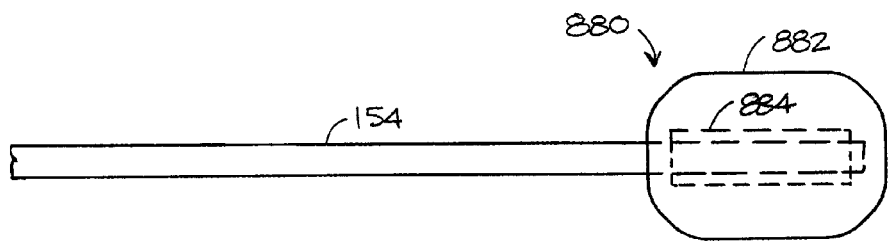
FIG. 52 is a side view of the leading section of a further alternate embodiment of a guide element, showing a chemical-property indicating medium thereof in a second example configuration.

According to a further aspect of the invention, there is shown in FIG. 52 a side view of an additional example embodiment 880 of a guide element with which a chemical-property indicating medium is incorporated on or near the leading section 154 thereof. Guide element 880 may generally be constructed as heretofore shown and described in connection with guide element 120 (FIG. 1), 610 (FIG. 30) or 630 (FIG. 33), with modifications as described in this section. As best seen in FIG. 52, one or more indicating elements 884 are provided on the outer surface of the leading section 154 of the guide element near the end thereof, each having a medium for visually indicating a chemical property. A swallowable weight 882 surrounds the indicating elements 884. Swallowable weight 882 is preferably constructed from a material that is soluble in stomach fluids, or disintegrates or becomes extremely soft when exposed to stomach fluids, or changes from a solid to liquid state when exposed to stomach fluids or to the temperature present in the body, as more fully explained in connection with the embodiment 630 of FIG. 33. After exposure to stomach fluids (or other fluids in the vicinity of the weight 882, the weight 882 dissolves, melts, ablates, or disintegrates, thereby exposing the indicating elements 884. When the guide element is withdrawn from the patient, the indicating elements are visually apparent and can be used to confirm that the guide element and nasogastric tube were properly inserted in the patient's stomach. Different, visually distinctive indicating elements may be used to indicate different chemical properties or values thereof, as described more fully in connection with embodiment 850 of FIG. 49. Any suitable indicating media could be used to implement the indicating elements 872, such as those described in connection with the embodiments 830 and 840 of FIGS. 45-46.

According to a further aspect of the invention, there is shown in FIG. 53 a flow diagram of a method 910 for use in positioning a nasogastric tube of the types shown and described in connection with FIGS. 43-50. Step 926 incorporates steps 310 or 310*a* through step 322 or 234*a* of FIG. 20, at the end of which, the guide element has been inserted through the nostrils and is ready to be swallowed by the patient.

In step 928, the guide element is swallowed by the patient. In step 930, the nasogastric tube is inserted along the guide element to an apparent terminal location. The apparent terminal location may be in the patient's stomach, as desired, or may be in some other undesired location, such as the lung. The implementation of step 930 may be further defined by optional substeps 932 and 934. In substep 932, inserting the nasogastric tube along the guide element is partially implemented by threading an opposite end of the guide element through a retaining structure of the nasogastric tube. In substep 934, inserting the nasogastric tube along the guide element is partially implemented by slidably moving the nasogastric tube along a path established by the guide element to an apparent terminal location.

In step 936, fluid from the vicinity of the terminal location is aspirated to expose a chemical-property indicating component to the fluid. In step 938, the user observes the indicator. In step 940, the user determines whether the indicator shows correct placement of the nasogastric tube. If the placement is determined to be correct, the method ends at step 942. If the placement is determined to be incorrect, the method continues in step 944, in which the user repositions the tube. The method then returns to step 936 and steps following.

According to a further aspect of the invention, there is shown in FIG. 54 a flow diagram of a method 960 for use in positioning a nasogastric tube in conjunction with a guide element of the types shown and described in connection with FIGS. 51-52. Step 926 incorporates steps 310 or 310*a* through step 322 or 234*a* of FIG. 20, at the end of which, the guide element has been inserted through the nostrils and is ready to be swallowed by the patient.

In step 978, the guide element is swallowed by the patient. In step 980, the nasogastric tube is inserted along the guide element to an apparent terminal location. The apparent terminal location may be in the patient's stomach, as desired, or may be in some other undesired location, such as the lung. The implementation of step 980 may be further defined by optional substeps 982 and 984. In substep 982, inserting the nasogastric tube along the guide element is partially implemented by threading an opposite end of the guide element through a retaining structure of the nasogastric tube. In substep 984, inserting the nasogastric tube along the guide element is partially implemented by slidably moving the nasogastric tube along a path established by the guide element to an apparent terminal location.

In step 986, a chemical-property indicating component of the guide element is exposed to fluid present near the terminal location. In step 988, the guide element is withdrawn, while the nasogastric tube remains in place. Removal of the guide element allows the indicating component to be viewed by a user.

In step 990, the user observes the indicator. In step 992, the user determines whether the indicator shows correct placement of the nasogastric tube. If the placement is determined to be correct, the method ends at step 994. If the placement is determined to be incorrect, the method continues in step 996, in which the nasogastric tube is removed. Then in step 998, the nasogastric tube is inserted again, using a guide element. Because the chemical-property indicating component will already have been exposed to fluids, it may be necessary to use a new guide element, or to renew the indicator on the previously-used guide element. Step 998 may incorporate steps 978 through 984, and the method may continue in step 986.

While the principles of the invention have been described above in connection with specific apparatus and applications, it is to be understood that this description is only an example and is not intended as a limitation on the scope of the invention. The above-described embodiments of the invention are merely examples of ways in which the invention may be carried out. Other ways may also be possible, and are within the scope of the following claims defining the invention.

What is claimed is:

1. A nasogastric tube insertion system for inserting a nasogastric tube in a human patient, comprising:
   a guide element for insertion into the patient's stomach;
   an inserter element adapted to engage an end of said guide element to enable insertion of said guide element through a patient's nasal passages and into the patient's oropharynx;
   wherein the guide element comprises:
      a thin tubular elongate element having a first end and a second end; and
      an inflatable swallowable weight affixed to said first end and adapted for fluid communication between said tubular element and interior space of said weight;
   said swallowable weight being adapted to deflate under control of a user;
   wherein the inserter element comprises a curved insertion section which conforms to an anatomy of the patient's nasal passages;
   wherein the curved insertion section is adapted to be inserted, with the guide element, through the patient's nasal passages and to the patient's oropharynx to position the first end of the guide element in the patient's oropharynx;
   wherein the guide element is separately insertable into the patient's stomach prior to insertion of the nasogastric tube.

2. The nasogastric tube insertion system of claim 1 wherein:
   said thin elongate element is adapted for slidable movement within a retaining structure of a nasogastric tube.

3. The nasogastric tube insertion system of claim 2 wherein:
   said swallowable weight is further adapted to change shape when it is deflated to thereby allow slidable movement of said swallowable weight through said retaining structure of said nasogastric tube.

4. A nasogastric tube insertion system, comprising:
   a guide element for insertion into a patient's stomach;
   an inserter element adapted to engage an end of said guide element to enable insertion of said guide element through a patient's nasal passages and into the patient's oropharynx;
   wherein the guide element comprises:
      a thin elongate element having a first end and a second end; and
      a swallowable weight affixed to said first end and adapted to ablate within a short period after the weight is inserted into the patient's stomach;
   wherein the inserter element comprises a curved insertion section which conforms to an anatomy of the patient's nasal passages;
   wherein the curved insertion section is adapted to be inserted, with the guide element, through the patient's nasal passages and to the patient's oropharynx to position the first end of the guide element in the patient's oropharynx;
   wherein the guide element is separately insertable into the patient's stomach prior to insertion of a nasogastric tube.

5. The nasogastric tube insertion system of claim 4 wherein said swallowable weight is adapted to ablate by dissolving in the presence of stomach fluids.

6. The nasogastric tube insertion system of claim 4 wherein said swallowable weight is adapted to ablate by disintegrating in the presence of stomach fluids.

7. The nasogastric tube insertion system of claim 4 wherein said elongate element further comprises attachment structures extending from the element to secure the weight to the element.

8. The nasogastric tube insertion system of claim 4 wherein said thin elongate element is adapted for slidable movement within a retaining structure of a nasogastric tube.

9. The nasogastric tube insertion system of claim 8 wherein:
   said thin elongate element is further adapted to allow slidable movement of said first end thereof through said retaining structure of said nasogastric tube after said weight has ablated.

10. The nasogastric tube insertion system of claim 8 wherein said retaining structure is a lumen extending most of the length of the nasogastric tube, and said thin elongate element is further adapted to allow slidable movement of said first end thereof through said retaining structure of said nasogastric tube after said weight has ablated.

11. A nasogastric tube insertion system, comprising:
   a guide element for insertion into a patient's stomach;
   an inserter element adapted to engage an end of said guide element to enable insertion of said guide element through a patient's nasal passages and into the patient's oropharynx;
   wherein the guide element comprises:
      a thin elongate element having a first end and a second end;
      a swallowable weight affixed to said first end; and
      a chemical-property indicating medium on said guide element adapted to provide a visual indication of a sensed chemical property;
   wherein the inserter element comprises a curved insertion section which conforms to an anatomy of the patient's nasal passages;
   wherein the curved insertion section is adapted to be inserted, with the guide element, through the patient's nasal passages and to the patient's oropharynx to position the first end of the guide element in the patient's oropharynx;

wherein the guide element is separately insertable into the patient's stomach prior to insertion of the nasogastric tube.

12. A nasogastric tube insertion system, comprising:
a nasogastric tube with an elongate tube body having a distal end and a proximal end;
a guide element for insertion into a patient's stomach;
an inserter element adapted to engage an end of said guide element to enable insertion of said guide element through a patient's nasal passages and into the patient's oropharynx;
wherein the guide element comprises:
  a thin elongate element having a first end and a second end; and
  a swallowable weight affixed to said first end;
wherein said nasogastric tube comprises:
  at least one lumen extending substantially from said distal end to said proximal end;
  an opening in said tube body near said distal end allowing fluid communication from said lumen to space exterior of the tube body; and
  a chemical-property indicating medium on said lumen adapted to receive fluid from said lumen to provide a visual indication of a sensed chemical property;
wherein the inserter element comprises a curved insertion section which conforms to an anatomy of the patient's nasal passages;
wherein the curved insertion section is adapted to be inserted, with the guide element, through the patient's nasal passages and to the patient's oropharynx to position the first end of the guide element in the patient's oropharynx;
wherein the guide element is separately insertable into the nauent's stomach prior to insertion of the nasogastric tube.

13. The nasogastric tube insertion system of claim 12 wherein said chemical-property indicating medium is adapted to provide a visual indication when pH of said fluid is below a predefined threshold.

14. The nasogastric tube insertion system of claim 12 wherein said chemical-property indicating medium is adapted to provide a visual indication when pH of said fluid is below about 5.0.

15. The nasogastric tube insertion system of claim 12 wherein said chemical property indicating medium includes phenolphthalein.

16. The nasogastric tube insertion system of claim 12 wherein said chemical property indicating medium comprises litmus.

17. The nasogastric tube insertion system of claim 12 wherein said chemical property indicating medium comprises a substrate bearing a pH indicator and said nasogastric tube further comprises a channel in fluid communication with said lumen for capturing said substrate.

18. The nasogastric tube insertion system of claim 12 wherein said chemical property indicating medium comprises a coating applied to an interior surface of said lumen.

19. The nasogastric tube insertion system of claim 12 wherein said chemical property indicating medium comprises a pH-indicator-bearing coating applied to an interior surface of said lumen.

20. A method for inserting a nasogastric tube in a patient comprising the steps of:

a. inserting a curved insertion section of an inserter element to aid in placing an end of a guide element into the patient's oropharynx, wherein the end of the guide element comprises a swallowable weight and is engaged with a distal tip of the curved insertion section, wherein the guide element comprises a thin elongate element;
b. releasing the end of the guide element from the inserter element;
c. causing the patient to swallow the swallowable weight of the guide element into the patient's stomach, wherein the guide element is separately inserted into the patient's stomach prior to insertion of the nasogastric tube; and
d. inserting the nasogastric tube along the guide element into the patient's stomach; and
e. withdrawing the guide element from the patient while the nasogastric tube remains in the patient's stomach.

21. The method of claim 20 wherein step e. thereof further comprises:
  e1. changing the shape of said guide element to allow the leading end of the guide element to pass through a retaining structure of the nasogastric tube.

22. The method of claim 21 wherein step e1. thereof further comprises:
  e1a. deflating a swallowable weight component of said guide element.

23. The method of claim 21 wherein step e1. thereof further comprises:
  e1a. ablating a swallowable weight component of said guide element by exposing it to stomach fluids.

24. The method of claim 23 wherein step e1a. thereof further comprises: e1a. dissolving the swallowable weight component of said guide element by exposing it to stomach fluids.

25. A method for positioning a nasogastric tube in a patient comprising the steps of:
a. inserting a curved insertion section of an inserter element to aid in placing an end of a guide element into the patient's oropharynx, wherein the end of the guide element comprises a swallowable weight and is engaged with a distal tip of the curved insertion section, wherein the guide element comprises a thin elongate element;
b. releasing the end of the guide element from the inserter element;
c. causing the patient to swallow the swallowable weight of the guide element into the patient's stomach, wherein the guide element is separately inserted into the patient's stomach prior to insertion of the nasogastric tube; and
d. inserting the nasogastric tube along the guide element to an apparent terminal location;
e. aspirating fluid from the vicinity of the apparent terminal location to expose a chemical-property indicator; and
f. repositioning the nasogastric tube if the chemical-property indicator does not indicate the nasogastric tube is properly positioned.

26. The method of claim 25 wherein step f. thereof further comprises:
  f1. repositioning the nasogastric tube if the chemical-property indicator indicates the pH of said fluid is over 5.0.

27. A method for positioning a nasogastric tube in a patient comprising the steps of:
a. inserting a curved insertion section of an inserter element to aid in placing an end of a guide element into the patient's oropharynx, wherein the end of the guide element comprises a swallowable weight and is engaged with a distal tip of the curved insertion section, wherein the guide element comprises a thin elongate element;

b. releasing the end of the guide element from the inserter element;
c. causing the patient to swallow the swallowable weight of the guide element, wherein the guide element is separately inserted into the patient's stomach prior to insertion of the nasogastric tube;
d. inserting the nasogastric tube along the guide element to an apparent terminal location;
e. exposing a chemical-property indicator to fluid from the vicinity of the apparent terminal location; and
f. removing the nasogastric tube if the chemical-property indicator does not indicate the nasogastric tube is properly positioned.

28. The method of claim 27 wherein step f. thereof further comprises:
f1. removing the nasogastric tube if the chemical-property indicator indicates the pH of said fluid is over 5.0.

29. The method of claim 27, further comprising the step of:
engaging an end of a guide element with a tip of a curved insertion section of an inserter element to aid in placing the end of the guide element through the patient's nasal passages and into the patient's oropharynx.

30. The method of claim 27, wherein the step of inserting the nasogastric tube comprises the steps of:
threading an opposite end of the guide element through a retaining structure of the nasogastric tube; and
slidably moving the nasogastric tube along a path established by the guide element into the patient's stomach.

31. The method of claim 27, further comprising the step of:
advancing said swallowable weight into said patient's oropharynx by applying to said guide element gentle longitudinal pressure in the direction of said patient's oropharynx.

* * * * *